United States Patent
Moaddeb et al.

(10) Patent No.: US 11,357,981 B2
(45) Date of Patent: Jun. 14, 2022

(54) SYSTEMS AND METHODS FOR CONTROLLING BLOOD PRESSURE

(71) Applicant: Adventus Ventures, LLC, Irvine, CA (US)

(72) Inventors: Shahram Moaddeb, Irvine, CA (US); Faizal Abdeen, Mission Viejo, CA (US); Rinda Sama, Laguna Niguel, CA (US)

(73) Assignee: Adventus Ventures, LLC, Irvine, CA (US)

( * ) Notice: Subject to any disclaimer, the term of this patent is extended or adjusted under 35 U.S.C. 154(b) by 0 days.

(21) Appl. No.: 16/288,605

(22) Filed: Feb. 28, 2019

(65) Prior Publication Data

US 2019/0269914 A1 Sep. 5, 2019

Related U.S. Application Data

(60) Provisional application No. 62/674,832, filed on May 22, 2018, provisional application No. 62/637,100, filed on Mar. 1, 2018.

(51) Int. Cl.
*A61B 5/318* (2021.01)
*A61N 1/36* (2006.01)
(Continued)

(52) U.S. Cl.
CPC ...... *A61N 1/36031* (2017.08); *A61B 5/02241* (2013.01); *A61B 5/0531* (2013.01);
(Continued)

(58) Field of Classification Search
CPC .. A61N 1/36031; A61N 7/00; A61B 5/02241; A61B 5/0402; A61B 5/0531; A61B 5/681; A61B 5/02416; A61B 8/04
See application file for complete search history.

(56) References Cited

U.S. PATENT DOCUMENTS 6,178,352 B1 * 1/2001 Gruzdowich ...... A61N 1/36014
607/44
6,379,310 B1 4/2002 Mori et al.
(Continued)

FOREIGN PATENT DOCUMENTS

AU 2017100994 A4 8/2017
AU 2018211196 B1 8/2018
(Continued)

OTHER PUBLICATIONS

Bang, S., Ryu, Y., Chang, S., Im, C., Bae, J., Gwak, Y., Yang, C., Kim, H., "Attenuation of hypertension by C-fiber stimulation of the human median nerve and the concept-based novel device," Scientific Reports, 2018, pp. 1-12, vol. 8, No. 14967, DOI: 10.1038/s41598-018-33402-1, www.nature.com/scientificreports.
(Continued)

*Primary Examiner* — Ankit D Tejani
*Assistant Examiner* — Joshua Brendon Solomon
(74) *Attorney, Agent, or Firm* — Blair Walker IP Services, LLC

(57) ABSTRACT

A system for controlling blood pressure includes a wearable interface having an internal contact surface, the wearable interface configured to at least partially encircle a first portion of a first limb of a subject, a sensing module carried by the wearable interface and configured to determine at least a change in blood pressure of the first limb of the subject, and an energy application module carried by the wearable interface and configured to apply energy of two or more types to the first limb of the subject.

25 Claims, 21 Drawing Sheets

(51) Int. Cl.
    *A61B 5/00*         (2006.01)
    *A61B 5/022*       (2006.01)
    *A61B 5/0531*     (2021.01)
    *A61B 8/04*         (2006.01)
    *A61N 7/00*         (2006.01)
    *A61B 5/024*       (2006.01)

(52) U.S. Cl.
    CPC .............. *A61B 5/318* (2021.01); *A61B 5/681* (2013.01); *A61B 8/04* (2013.01); *A61N 7/00* (2013.01); *A61B 5/02416* (2013.01)

(56) References Cited

U.S. PATENT DOCUMENTS

| | | | |
|---|---|---|---|
| 9,649,511 | B2 | 5/2017 | Nonogaki |
| 9,789,315 | B2 | 10/2017 | Dacey, Jr. et al. |
| 10,052,041 | B2 | 8/2018 | Banet et al. |
| 10,127,367 | B2 | 11/2018 | Cherry et al. |
| 2001/0020177 | A1 | 9/2001 | Gruzdowich et al. |
| 2006/0195035 | A1 | 8/2006 | Sun |
| 2010/0152545 | A1* | 6/2010 | Ramsay ............... A61B 5/0002 600/301 |
| 2012/0245483 | A1 | 9/2012 | Lundqvist |
| 2014/0214111 | A1 | 7/2014 | Greiner et al. |
| 2014/0214112 | A1 | 7/2014 | Greiner et al. |
| 2014/0214113 | A1 | 7/2014 | Greiner et al. |
| 2014/0214115 | A1 | 7/2014 | Greiner et al. |
| 2014/0214116 | A1 | 7/2014 | Peterson et al. |
| 2014/0214117 | A1 | 7/2014 | Greiner et al. |
| 2014/0214118 | A1 | 7/2014 | Greiner et al. |
| 2014/0214119 | A1 | 7/2014 | Greiner et al. |
| 2014/0214124 | A1 | 7/2014 | Greiner et al. |
| 2014/0214125 | A1 | 7/2014 | Greiner et al. |
| 2014/0214126 | A1 | 7/2014 | Greiner et al. |
| 2014/0214127 | A1 | 7/2014 | Greiner et al. |
| 2014/0214128 | A1 | 7/2014 | Peterson et al. |
| 2014/0214133 | A1 | 7/2014 | Thenuwara et al. |
| 2014/0214144 | A1 | 7/2014 | Peterson et al. |
| 2015/0012056 | A1 | 1/2015 | Greiner et al. |
| 2015/0119654 | A1* | 4/2015 | Martin ................. A61B 5/6824 600/301 |
| 2015/0148864 | A1 | 5/2015 | Peterson et al. |
| 2015/0157867 | A1* | 6/2015 | Ternes ............... A61N 1/36114 607/62 |
| 2015/0190307 | A1 | 7/2015 | Ehrenreich et al. |
| 2015/0245483 | A1 | 8/2015 | Miyasaka |
| 2015/0321000 | A1* | 11/2015 | Rosenbluth ............ A61N 1/025 607/48 |
| 2016/0001096 | A1 | 1/2016 | Mishelevich |
| 2016/0007925 | A1 | 1/2016 | Mirov et al. |
| 2016/0226542 | A1 | 8/2016 | Tran et al. |
| 2016/0331620 | A1 | 11/2016 | Kazanchyan et al. |
| 2017/0014625 | A1 | 1/2017 | Rosenbluth et al. |
| 2017/0021171 | A1* | 1/2017 | Perez .................... A61N 1/0476 |
| 2017/0095670 | A1 | 4/2017 | Ghaffari et al. |
| 2017/0157398 | A1 | 6/2017 | Wong et al. |
| 2017/0165486 | A1 | 6/2017 | Harry et al. |
| 2017/0172434 | A1* | 6/2017 | Amelard .............. A61B 5/7278 |
| 2017/0173262 | A1 | 6/2017 | Veltz |
| 2017/0266443 | A1 | 9/2017 | Rajguru et al. |
| 2018/0263510 | A1 | 9/2018 | Cronin et al. |
| 2018/0266820 | A1 | 9/2018 | De Panisse et al. |
| 2019/0001129 | A1* | 1/2019 | Rosenbluth .......... A61N 1/0476 |
| 2019/0159676 | A1 | 5/2019 | Murphy et al. |
| 2019/0358464 | A1 | 11/2019 | Volosin et al. |
| 2020/0121258 | A1 | 4/2020 | Zhu et al. |
| 2021/0101007 | A1 | 4/2021 | Hamner et al. |
| 2021/0113834 | A1 | 4/2021 | Wong et al. |

FOREIGN PATENT DOCUMENTS

| | | | | |
|---|---|---|---|---|
| JP | 2009136585 | A2 | 6/2009 | |
| JP | 6373647 | B2 | 8/2018 | |
| KR | 10-1349680 | B1 | 1/2014 | |
| WO | WO2015/099090 | A1 | 2/2015 | |
| WO | WO-2017023864 | A1 * | 2/2017 | ............. A61B 5/486 |
| WO | WO2018/039458 | A1 | 3/2018 | |
| WO | WO2019/046180 | A1 | 3/2019 | |

OTHER PUBLICATIONS

"20 minutes of ultrasound to the forearm cuts high blood pressure," ScienceDaily. ScienceDaily, Jul. 27, 2016. <www.sciencedaily.com/releases/2016/07/160727124910.htm>. (2 pages).
"Blood pressure can significantly drop by applying 20 minutes of ultrasound to the forearm of type II diabetes patients with treatment-resistant hypertension, according to research from Japan's Tohoku University," printed off internet Nov. 17, 2018—Asia Research News website (2 pages).
"Volemer A69 Smart Bracelet Blood Pressure Touch Vibrating Bracelet Wrist Band Smart Watch With Heart Rate Alarm Adult Pk ID107," printed off internet Feb. 26, 2018 (1 page).
PCT International Search Report and Written Opinion for PCT/US2019/020240, Adventus Ventures, LLC, Forms PCT/ISA/220, 210, and 237 dated May 23, 2019 (12 pages).
JP6373647B2 Machine translation (37 pages).
KR101349680B1 Machine translation (10 pages).
Extended European Search Report dated Mar. 17, 2021, in EP App. No. 19760770.8 filed Mar. 1, 2019 (9 pages).
Rajput, A., Offord, K., Beard, C., Kurland L. "Essential tremor in Rochester, Minnesota: a 45-year study." Journal of Neurology, Neurosurgery, and Psychiatry 47: 466-470 (1984).
Putzke, J., Whaley, N., Baba, Y., Wszolek, Z., Uitti, R. "Essential tremor: predictors of disease progression in a clinical cohort." Journal of Neurology, Neurosurgery, and Psychiatry 77: 1235-1237 (2006).
"Get the most out of home blood pressure monitoring: Checking your blood pressure at home is an important part of managing high blood pressure. Find out how to use home monitors accurately," by the Mayo Clinic Staff (6 pages) Downloaded from internet Feb. 23, 2021.
Figueroa A., Gil R., Wong A., Hooshmand S., Parks., Vicil F., Sanchez-Gonzalez M., "Whole-body vibration training reduces arterial stiffness, blood pressure and sympathovagal balance in young overweight/obese women," Hypertension Research, Feb. 23, 2012, pp. 667-672, vol. 35, www.nature.com/hr.
Poenaru D., Cinteza D., Petrusca I., Cioc L., Dumitrascu D., "Local Application of Vibration tn Motor Rehabilitation—Scientific and Practical Considerations," MAEDICA—A Journal of Clinical Medicine, 2016, pp. 227-231, vol. 11, No. 3, https://www.maedica.ro/.
Shekarforoush S., Naghii M., "Whole-Body Vibration Training Increases Myocardial Salvage Against Acute Ischemia in Adult Male Rats," Arquivos Brasileiros de Cardiologia, 2019, pp. 32-37, vol. 112, No. 1, https://abccardiol.org/en/.

\* cited by examiner

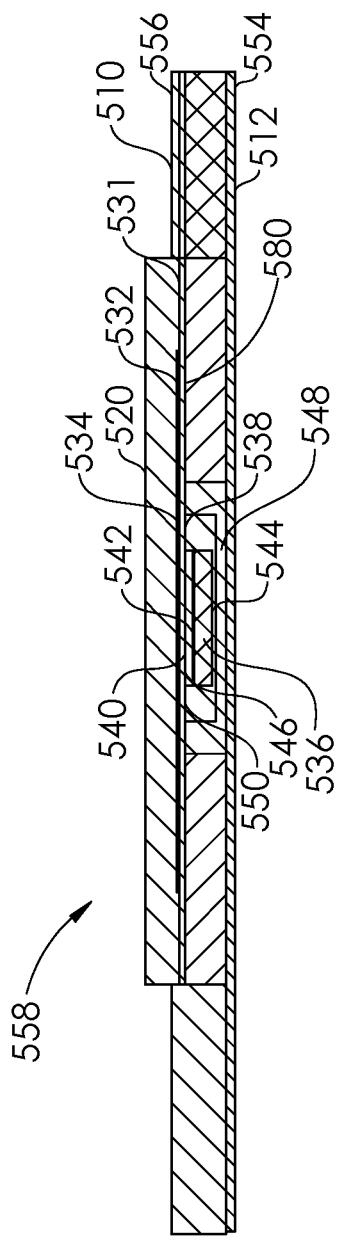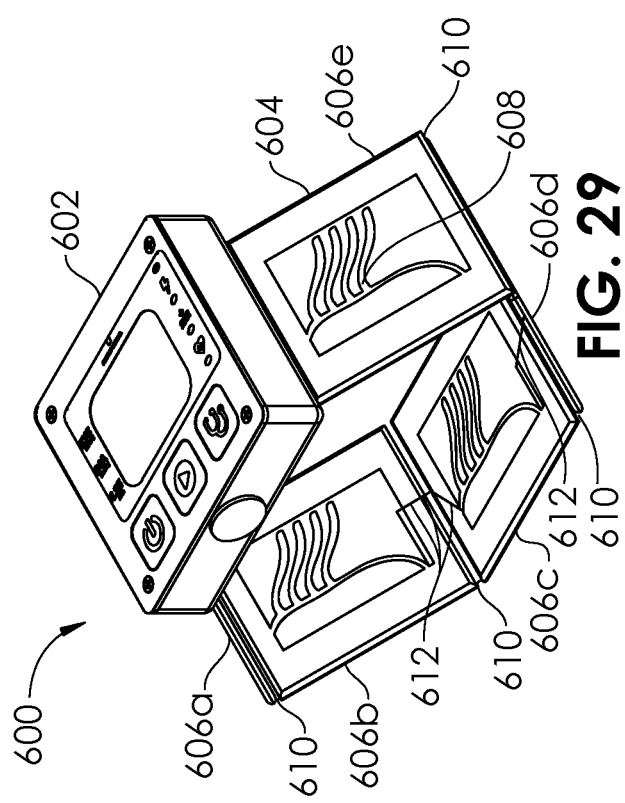

SYSTEMS AND METHODS FOR CONTROLLING BLOOD PRESSURE

INCORPORATION BY REFERENCE TO ANY PRIORITY DOCUMENTS

This application claims the benefit of priority to U.S. Provisional Application No. 62/637,100, filed on Mar. 1, 2018, and U.S. Provisional Application No. 62/674,832, filed on May 22, 2018, both of which are herein incorporated by reference in their entirety for all purposes. Priority is claimed pursuant to 35 U.S.C. § 119.

BACKGROUND OF THE INVENTION

Embodiments of the present invention relate to systems and methods for controlling blood pressure in living subjects.

SUMMARY OF THE INVENTION

In a first embodiment of the present disclosure, a system for controlling blood pressure includes a wearable interface having an internal contact surface, the wearable interface configured to at least partially encircle a first portion of a first limb of a subject, a sensing module carried by the wearable interface and configured to determine at least a change in blood pressure of the first limb of the subject, and an energy application module carried by the wearable interface and configured to apply energy of two or more types to the first limb of the subject.

In another embodiment of the present disclosure, a system for controlling blood pressure includes a wearable interface having an internal contact surface, the wearable interface configured to at least partially encircle a first portion of a limb of a subject, a sensing module carried by the wearable interface and configured to determine at least a change in blood pressure of the limb of the subject, wherein the sensing module includes at least one sensor for determining a flow characteristic, and an energy application module carried by the wearable interface and configured to apply energy to the limb of the subject.

In yet another embodiment of the present disclosure, a method for controlling blood pressure of a subject includes providing a system for controlling blood pressure including a wearable interface having an internal contact surface, the wearable interface configured to at least partially encircle a first portion of a first limb of a subject, a sensing module carried by the wearable interface and configured to determine at least a change in blood pressure of the first limb of the subject, and an energy application module carried by the wearable interface and configured to apply energy of two or more types to the first limb of the subject, placing the system on an arm of a patient, measuring blood pressure with the system, and applying energy with the system to a median nerve of the subject.

In still another embodiment of the present disclosure, a method for controlling blood pressure of a subject includes providing a system for controlling blood pressure including a wearable interface having an internal contact surface, the wearable interface configured to at least partially encircle a first portion of a first limb of a subject, a sensing module carried by the wearable interface and configured to determine at least a change in blood pressure of the first limb of the subject, and an energy application module carried by the wearable interface and configured to apply energy of two or more types to the first limb of the subject, placing the system on an arm of a patient, measuring blood pressure with the system, and applying energy with the system to a radial nerve of the subject.

In yet another embodiment of the present disclosure, a method for controlling blood pressure of a subject includes providing a system for controlling blood pressure including a wearable interface having an internal contact surface, the wearable interface configured to at least partially encircle a first portion of a first limb of a subject, a sensing module carried by the wearable interface and configured to determine at least a change in blood pressure of the first limb of the subject, and an energy application module carried by the wearable interface and configured to apply energy of two or more types to the first limb of the subject, placing the system on an arm of a patient, measuring blood pressure with the system, and applying energy with the system to a ulnar nerve of the subject.

BRIEF DESCRIPTION OF THE DRAWINGS

FIG. 28 is a cross-sectional view of the wearable blood control system of FIG. 22, taken through line 28-28.

FIG. 29 is a perspective view of a wearable blood pressure control system, according to an embodiment of the present disclosure.

DETAILED DESCRIPTION OF THE ILLUSTRATED EMBODIMENTS

Hypertension (high blood pressure) affects a large section of the world's population, with estimates of between 16% to 37% of the population affected. Hypertension can be persistent or transient, but in either case, is a significant factor which commonly increases morbidity and mortality, both on its own and in conjunction with other maladies. Hypertension is thought to be a factor in about 18% of deaths worldwide. Hypertension is of concern in all parts of the world, among most population subgroups. The lowering of mean blood pressure by a small amount (e.g., about 5 mm Hg or more), can significantly reduce stroke or other cardiovascular events.

Figure 1:
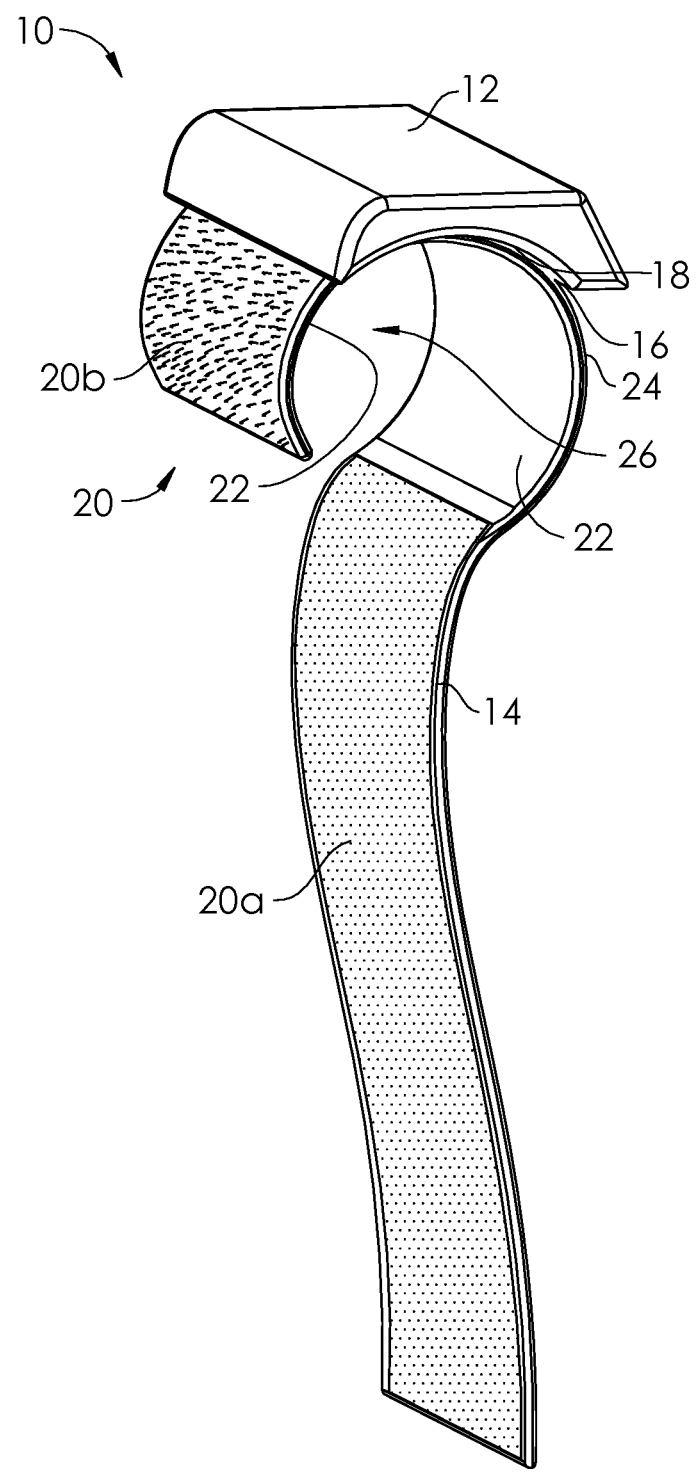
FIG. 1 is a perspective view of a wearable blood pressure control system, according to an embodiment of the present disclosure.

A simple, wearable device that can sense increases in blood pressure, and in response, deliver blood pressure lowering therapy is described herein, according to several embodiments. FIG. 1 illustrates a wearable blood pressure control system 10 configured for placement on the wrist of a patient. The wearable blood pressure control system 10 comprises a housing 12 and a band 14 coupled to an underside 16 of the housing 12. The wearable blood pressure control system 10 is shown in FIG. 1 in an unfastened condition. The band 14 is secured to the underside 16 of the housing 12 by epoxy or adhesive 18. In other embodiments, the band 14 may be secured by fasteners, sewing, fusing, or may slide through slits or elongate spaces in the housing 12. The band 14 is configured to wrap around the wrist of a user/patient and secure to itself by use of a hook and loop (Velcro®-type) system 20. The loop surface 20a on an interior of a portion of the band 14 secures to the hook surface 20b on an exterior portion of the band 14. The band may be provided in a number of different sizes to optimize placement on a particularly-sized patient (e.g., small, medium, large or pediatric, adult). An inflatable cuff 22 extends around a circumferential path 24 encircling an interior 26 of the band 14. In some embodiments, the band 14 may be configured to be worn like a watch or a bracelet, and may be configured to partially or fully encircle a limb (e.g., arm) at a portion (e.g., wrist). The hook and loop system 20 may be replaced in alternative embodiments by a button closure, a snap closure, an adhesive closure, or a magnetic closure.

Figure 2:
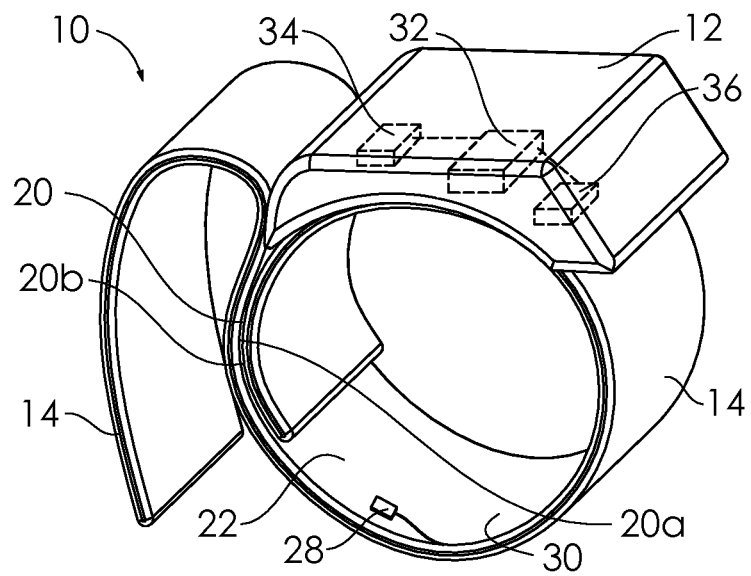
FIG. 2 is a perspective view of the wearable blood pressure control system of FIG. 1 in a fastened, unexpanded condition.
Figure 3:
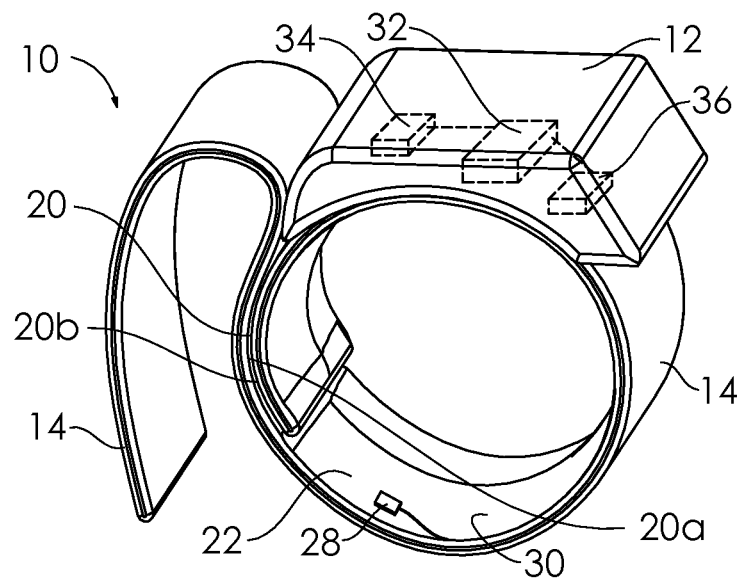
FIG. 3 is a perspective view of the wearable blood pressure control system of FIG. 1 in a fastened, partially expanded condition.
Figure 4:
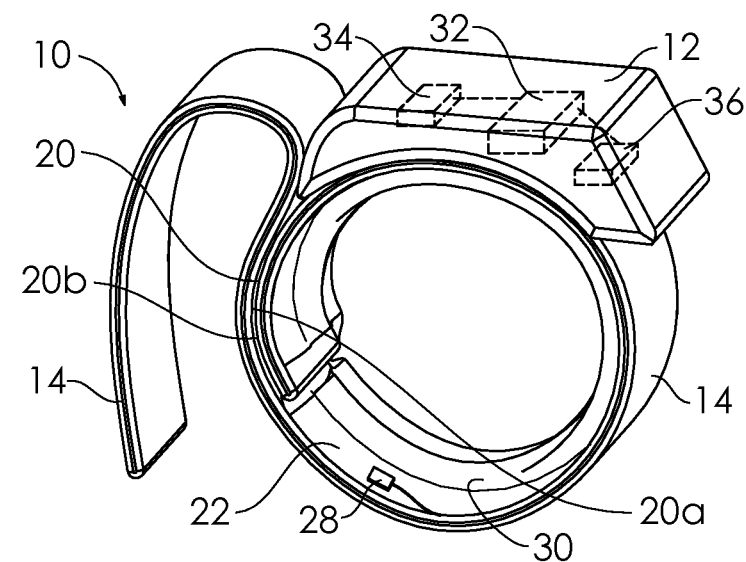
FIG. 4 is a perspective view of the wearable blood pressure control system of FIG. 1 in a fastened, substantially expanded condition.

FIG. 2 illustrates the wearable blood pressure control system 10 in a fastened condition, with the loop surface 20a secured to the hook surface 20b. No arm of a user is shown in FIGS. 2-4 in order to better show the activity of the inflatable cuff 22. A sensor 28 is carried on an interior face 30 of the band 14, and is configured to sense one or more cardiovascular parameter, such as heart rate, heart rate variability, electrocardiogram (ECG), including any measured arrythmias, or blood pressure. In some embodiments, the sensor 28 may comprise a pulse wave sensor. The pulse wave sensor may comprise CMOS (complementary metal-oxide-semiconductor) technology. In some embodiments, the sensor 28 may comprise an ultrasound transducer. The ultrasound transducer may comprise two or more piezoelectric elements. The ultrasound transducer may be configured to be operated as a Doppler transducer. In alternative embodiments, the sensor 28 may comprise one or more optical sensor for performing photoplethysmography (PPG). A controller 32 within the housing 12 is configured to receive signals from the sensor 28. The controller 32 may comprise a microcontroller. The controller 32 may be coupled to a transceiver 34, configured to communicate wirelessly to a cellular phone, smart phone, or other personal communication device, including a chip implanted in a user's body, or carried on a portion of the user's body or clothing. The data monitoring, and data analysis, are thus capable of being performed remotely. The controller 32 can be configured to analyze data from the sensor 28 to determine the presence of conditions including bradycardia, tachycardia, atrial arrythmia such as atrial fibrillation or atrial flutter, or ventricular arrythmia such as ventricular tachycardia. The identification of any of these phenomena may be based on real time analysis of heart rate, heart rate variability, or ECG amplitude. The sensor 28 may be capable of sensing more than one cardiovascular parameter. For example, the sensor 28 may be configured to sense blood pressure and heart rate, or blood pressure and heart rate variability, or may be configured to obtain an electrocardiogram and measure blood pressure. In some embodiments, the sensor 28 may comprise two or more sensors. In some embodiments, the two or more sensor may comprise a first sensor for measuring a first cardiovascular parameter, and a second sensor for measuring a second cardiovascular parameter, different from the first cardiovascular parameter.

Changes in heart rate variability, for example a reduction in heart rate variability, have been shown to have some predictive capability of mortality after myocardial infarction. A more continual or even continuous measurement of blood pressure using the sensor 28 allows an awareness of how the heart responds to the changing environment during each day. Rather than focusing on simple lowering average (e.g., mean) blood pressure values, there may be more protection against heart disease by achieving hour-to-hour, day-to-day controlled blood pressure values over time. These data may be used to help physicians make more informed decisions relating to the treatment of hypertension, and overall treatment of the heart. The wearable blood pressure control system 10 is configured to monitor blood pressure throughout the day at different activities (eating, drinking, dieting, fasting, exercising, sleeping, walking, standing). Data obtained by the sensor 28 may be used intelligently to apply treatment based on specific or custom patient needs, and may be guided by saved information related to optimum times to apply the therapy.

The inflatable cuff 22 may be operated as a sphygmomanometer cuff, configured to determine blood pressure of the user. The transceiver 34 may comprise a wifi antenna. An actuator 36, coupled to the controller 32 is configured to receive signals from the controller 32 to cause the inflatable cuff 22 to expand. The actuator 36 may comprise a pneumatic pump configured to increase air pressure within the inflatable cuff 22. The inflatable cuff 22 is shown in FIG. 2 in a substantially unexpanded condition. The inflatable cuff 22 in FIG. 3 is shown in a partially expanded condition. The inflatable cuff 22 in FIG. 4 is shown in a substantially expanded condition. The inflatable cuff 22 may also be expanded by the controller 32 via the actuator 36 in order to apply a therapeutic compression on the wrist of the patient. In a first embodiment, the sensor 28 is configured to sense blood pressure, and the inflatable cuff 22 is configured to apply therapeutic compression. In a second embodiment, the sensor 28 is configured to sense at least one parameter related to blood pressure, and the inflatable cuff 22 is configured to sense at least one parameter related to blood pressure, and to also apply therapeutic compression. In a third embodiment, the inflatable cuff 22 is configured to sense blood pressure and to apply therapeutic compression, and the sensor 28 is configured to sense one or more cardiovascular parameter other than blood pressure. In a fourth embodiment, the sensor 28 is configured to sense at least one parameter related to blood pressure, the inflatable cuff 22 is configured to sense at least one parameter related to blood pressure, and some other element (not shown) is configured to apply a therapy for reducing blood pressure.

Figure 5:
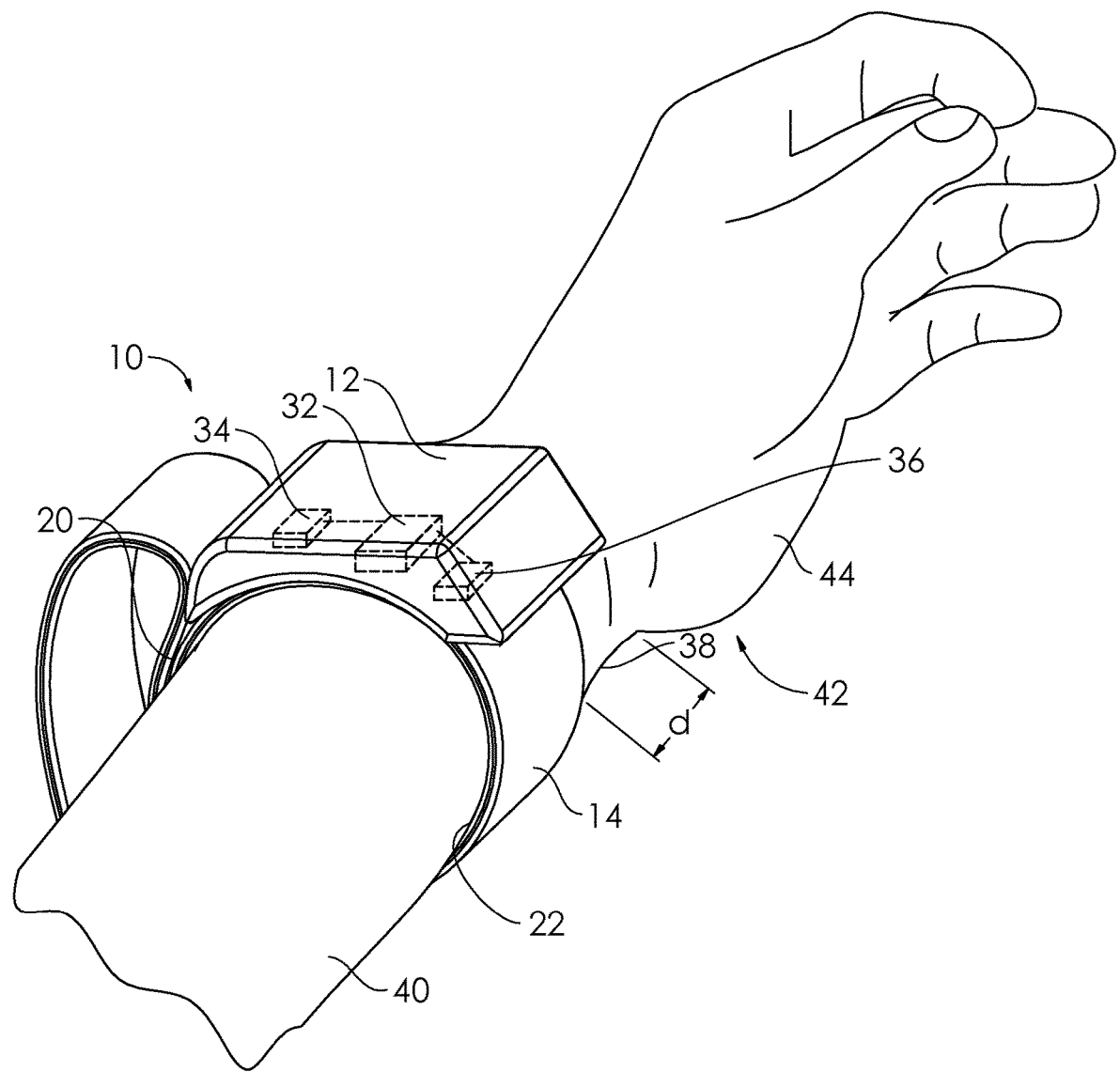
FIG. 5 is a perspective view of the wearable blood pressure control system of FIG. 1 in use on the wrist of a user.

In FIG. 5, the wearable blood pressure control system 10 is in use, in place on the wrist 38 of the arm 40 of a user 42. The band 14 may be secured immediately adjacent the hand 44 of the user 42, or may be attached around the wrist 38 (or other portion of the arm 40) a distance d away from the hand 44, for example 0.5 cm, 1 cm, 2 cm, 5 cm, 10 cm, or 15 cm, or any distance between 0 cm and 15 cm.

Figure 8:
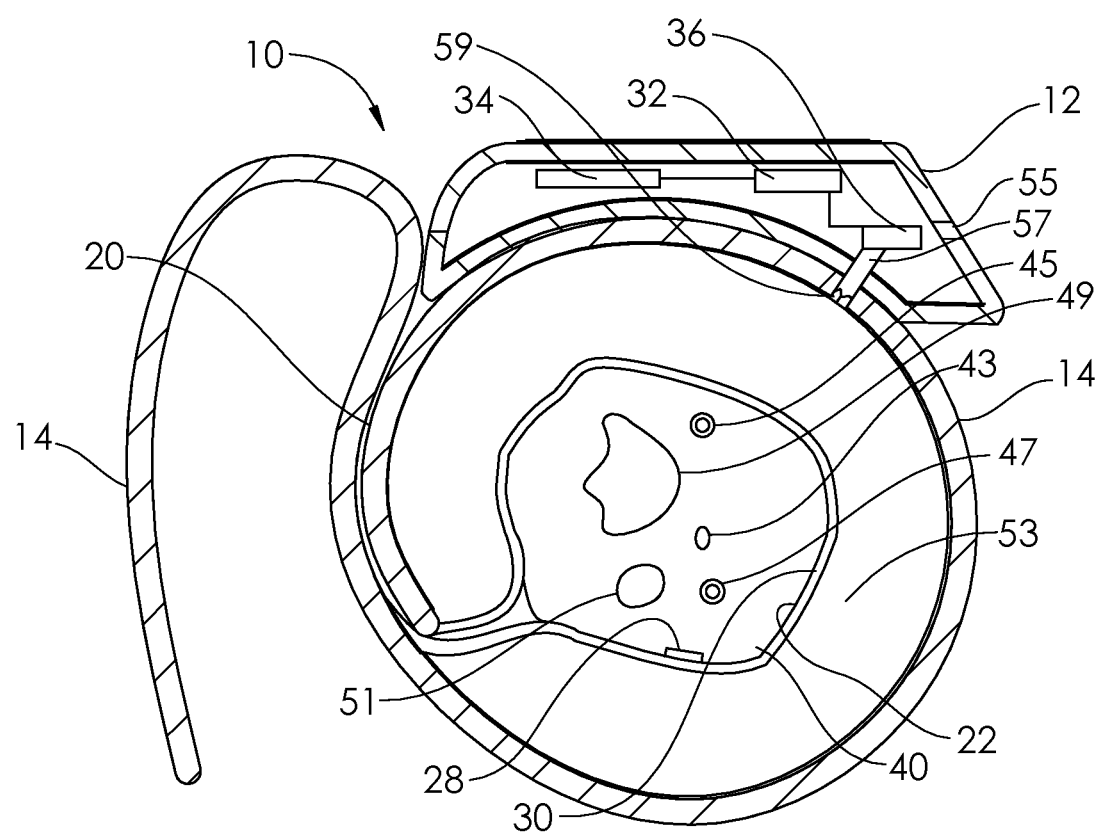
FIG. 8 is a cross-section of the wearable blood pressure control system of FIG. 1 in use on the wrist of a user.

Turning to FIG. 8, wearable blood pressure control system 10 is shown coupled to an arm 40 of the user 42. Anatomical elements such as the radius 49, ulna 51, radial artery 45 and ulnar artery 47 are shown in relation to the band 14 and housing 12. The positioning of the wearable blood pressure control system 10 in relation to the arm 40 in FIG. 8 is one of many possible choices. The wearable blood pressure control system 10 may be oriented differently (e.g., circumferentially/rotationally and/or longitudinally/axially) if a different juxtaposition between the sensor 28 and one or more of the arteries 45, 47 or between the inflatable cuff 22 and one or more of the arteries 45, 47 is desired. An interior 53 of the inflatable cuff 22 is inflated by air pressurized by the actuator 36, which is free to enter into the housing 12 (or exit out of the housing 12) via a vent hole 55. The air is forced by the actuator 36 into the inflatable cuff 22 through an access conduit 57 having a valve 59. The valve 59 is configured to maintain air pressure in the interior 53 of the inflatable cuff 22. The actuator 36 and/or valve 59 are also configured to allow air to exit through the valve 59 when it is desired to lower the air pressure inside the interior 53 of the inflatable cuff 22.

Figure 6:
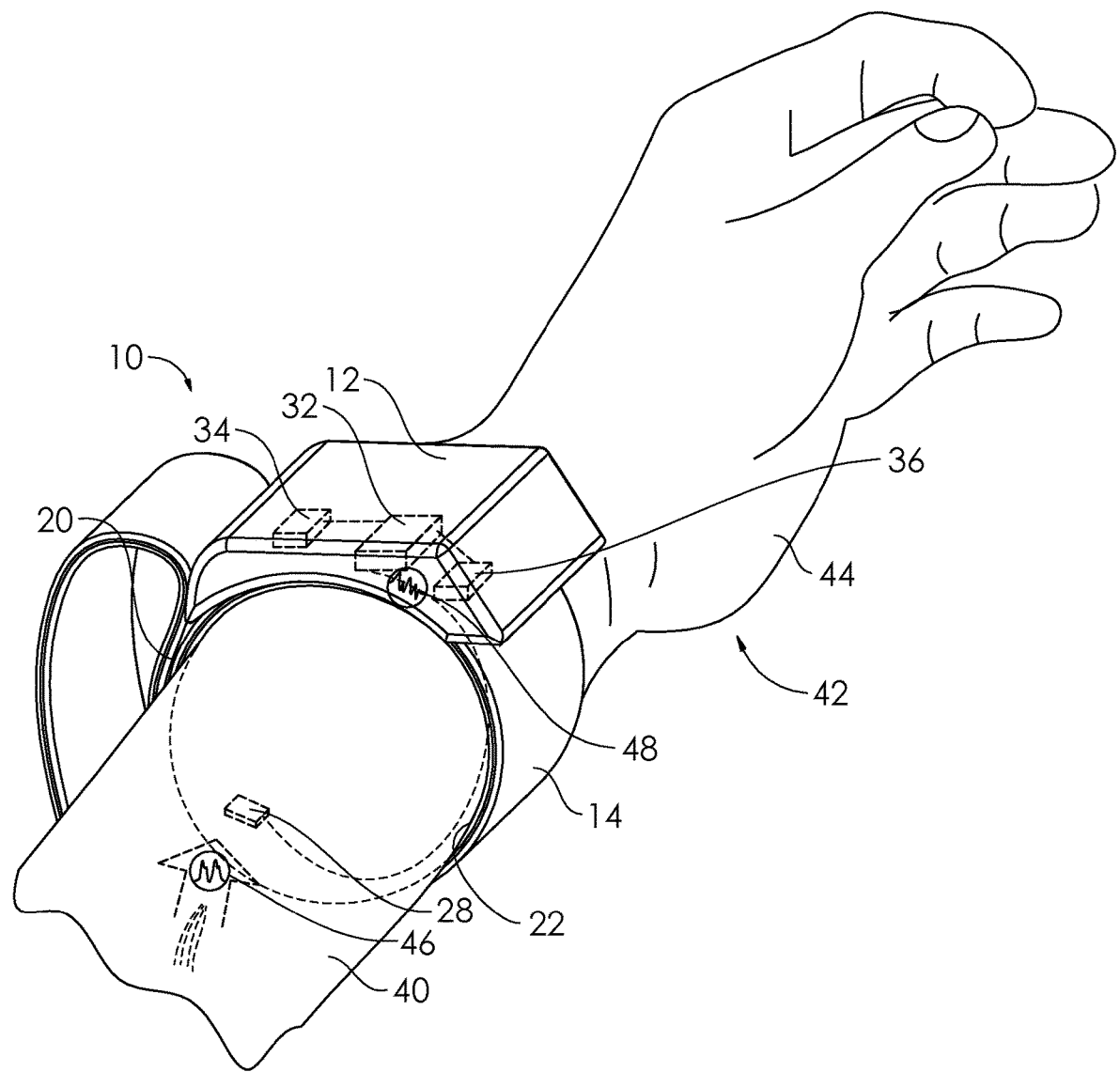
FIG. 6 is a perspective view of the wearable blood pressure control system of FIG. 1 during the measurement of blood pressure.
Figure 7:
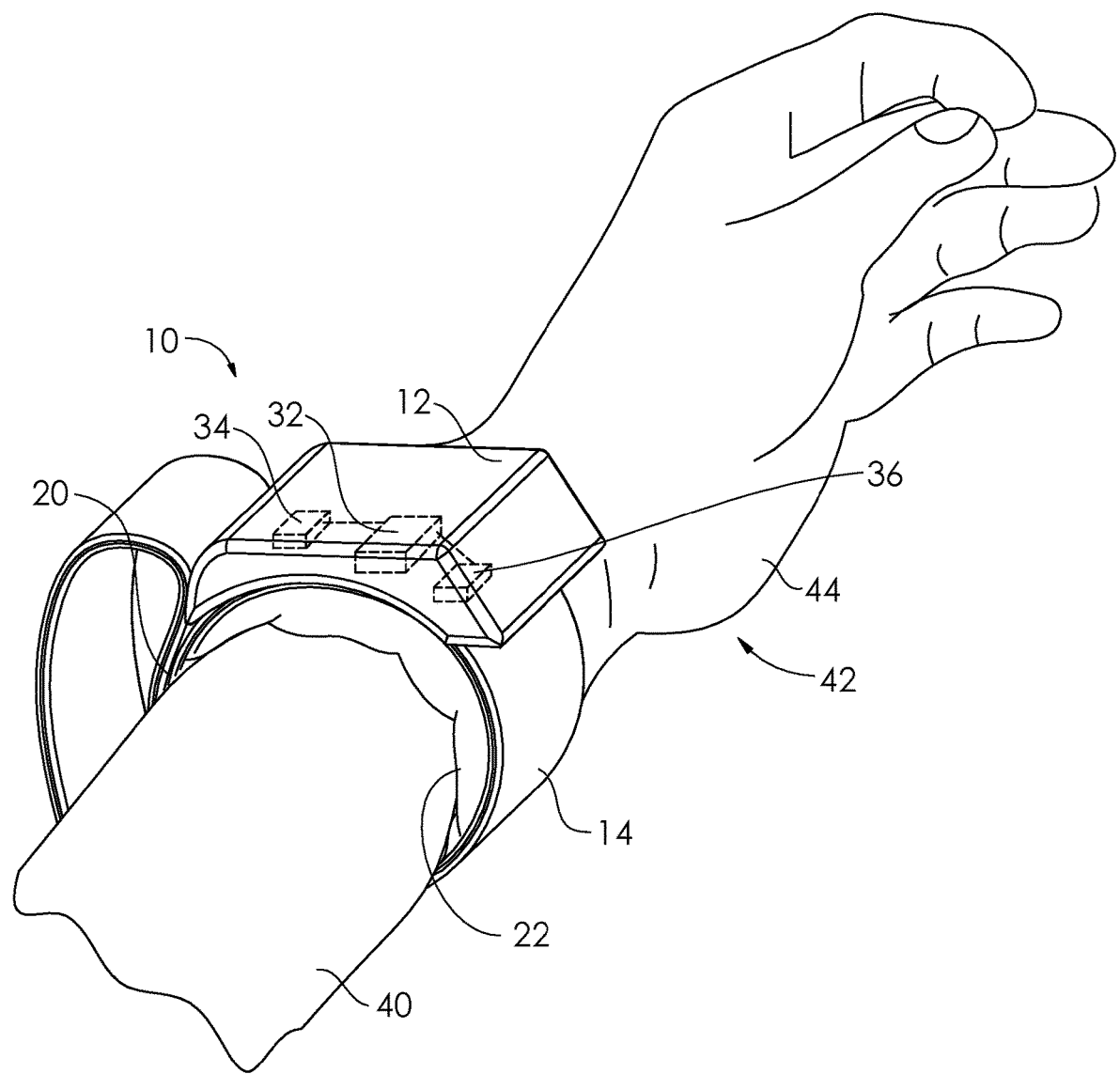
FIG. 7 is a perspective view of the wearable blood pressure control system of FIG. 1 during activation in response to a detected change in blood pressure.

In FIG. 6, the sensor 28, in use, senses the blood pressure 46 of the user 42. The blood pressure 46 may be measured continuously or in a series of samples. The blood pressure 46 may be treated as a systolic pressure over a diastolic pressure, or may be treated as a mean arterial pressure (MAP). The sensor 28 outputs a signal 48 proportional to the blood pressure 46 that is received by the controller 32. In FIG. 7, the controller 32 commands the actuator 36 to expand the inflatable cuff 22. In embodiments wherein the inflatable cuff 22 is configured to be used as a sphygmomanometer cuff, the controller 32 controls the inflation of the inflatable cuff 22 by the actuator 36 so that the interior 53 (FIG. 8) is pressurized to a starting pressure $P_s$ that is above the expected maximum systolic arterial pressure. The controller 32 then commands the actuator 36 and/or valve 59 to allow the release of air from the interior 53 at a particular rate, so that the pressure of the interior 53 is reduced over a time period T to a pressure $P_f$ that is below expected minimum arterial diastolic pressure. The oscillometric sensing (e.g., by the sensor 28) of the occlusion and subsequent opening up of one or more arteries can also be used to determine the actual systolic and diastolic pressures, and the pressurization and depressurization of the inflatable cuff 22 can be controlled by these data (e.g., via the controller 32).

In embodiments wherein the inflatable cuff 22 is configured to be used as a therapeutic compression element, the controller 32 controls the inflation of the inflatable cuff 22 by the actuator 36 so that the interior 53 is pressurized to a desired treatment inflation pressure $P_t$. The therapeutic compression imparted on the arm 40 by the inflatable cuff 22 can be directed to apply stresses to the median nerve 43 (FIG. 8). Stimulation of the median nerve by application of energy, such as compression, can help lower blood pressure, via a known neural pathway, which may include the central nervous system (CNS). In some cases, the reduction in blood pressure may be achieved via down-regulation of sympathetic outflow. In some embodiments, the inflatable cuff 22 may be configured to be used both as a sphygmomanometer cuff and as a therapeutic compression element.

Figure 9:
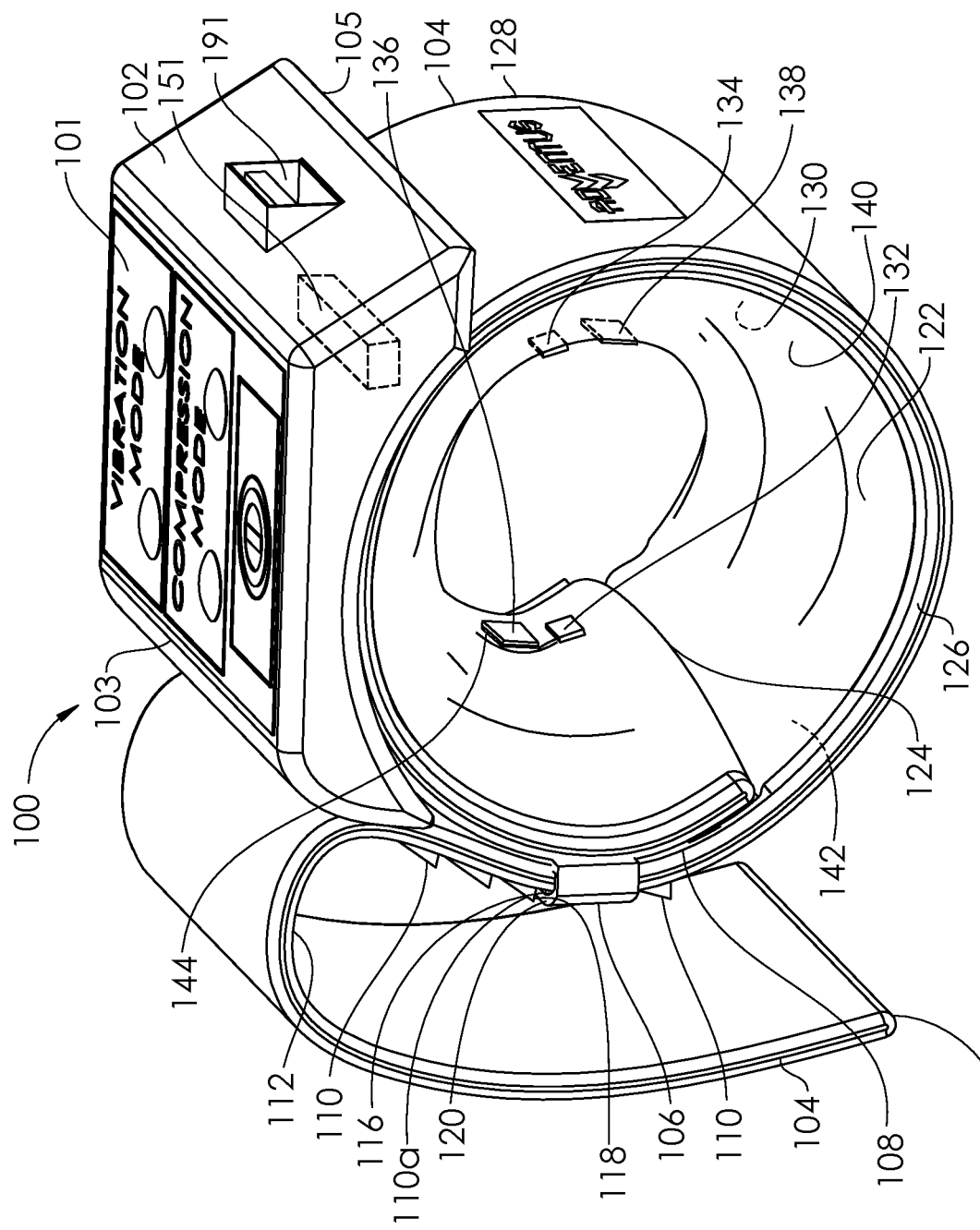
FIG. 9 is a perspective view of a wearable blood pressure control system, according to an embodiment of the present disclosure.

FIG. 9 illustrates a wearable blood pressure control system 100 configured for placement on the wrist of a patient. The wearable blood pressure control system 100 comprises a housing 102 and a band 104 coupled to an underside 105 of the housing 102. The wearable blood pressure control system 100 is shown in FIG. 9 in a fastened condition, though without the arm 40 visible, in order to better show features of the wearable blood pressure control system 100. A loop 106 is secured to a first portion 108 of the band 104 and a series of rubber wedges 110 are carried by a second portion 112 of the band 104. To attach the wearable blood pressure control system 100 to the user's wrist 38, the user 42 (or a person aiding the user 42) slips first end 114 of the band 104 through an opening 116 of the loop 106 and, while applying traction on the first end 114, pulls one or more of the wedges 110 through the opening 116 of the loop 106, until the band 104 is at a comfortable tightness around the user's wrist 38. A flat edge 118 of one of the wedges 110a, abuts an edge 120 of the loop 106, locking it in place. To remove the band 104, the band 104 is forced in the opposite direction, temporarily (elastically) deforming the wedges 110 as they are pulled through the opening 116 in the loop 106 (or deforming the loop 106) and/or temporarily (elastically) deforming the loop 106. Alternatively, a hook and loop system 20, like that of the wearable blood pressure control system 10 of FIG. 1 may be used. The wearable blood pressure control system 100 also includes a user interface 101 on a visible surface 103 of the housing 102.

The wearable blood pressure control system 100 includes a cuff 122 extending circumferentially within the band 104 between a second end 124 of the band 104 and the first portion 108. The cuff 122 is secured to the band 104 along a first edge 126 and a second edge 128, each running circumferentially around an internal periphery of the band 104. The cuff 122 may be secured to the band 104 at the first and second edges 126, 128 by adhesive, epoxy, or hotmelt, or may be sewn, stapled, or secured with other fastening means. The cuff 122, as named, represents an outer layer, though it is an inner portion of a circle when attached. As shown in FIG. 9, the cuff 122 is configured to have an interior space 130 that is inflatable.

The cuff 122 carries a pair of sensing elements 132, 134 and a pair of vibration elements 136, 138. The vibration elements 136, 138 may comprise piezoelectric crystals, and may comprise quartz, artificial quartz, or PZT (lead zirconate titanate) ceramics. The vibration elements 136, 138 may be configured to vibrate at ultrasound frequencies of between about 20 kHz and about 1 MHz, or between about 20 kHz and about 700 kHz, or between about 20 kHz and about 500 kHz, or between about 25 kHz and about 500 kHz, or between about 30 kHz and about 200 kHz, or between about 100 kHz and about 300 kHz. Frequencies between about 20 kHz and about 700 kHz can be very effective at stimulating nerves, such as the median nerve 43 in the arm 40, or the radial nerve or ulnar nerve. Ultrasound can serve to stimulate several physiological processes that can aid the reduction of blood pressure. Ultrasound energy application is capable of dilating blood vessels, such as arteries, and can thus improve blood perfusion. Via sensory feedback, the brain is signaled, in turn, to modify other physiological functions, to further reduce blood pressure. Thus, the vibration elements 136, 138, when constructed of an appropriate material and having an appropriate thickness to vibrate at one or more frequencies in the 20-700 kHz range, may be configured to stimulate the median nerve 43 via vibration. The applied vibration to the median nerve 43 will be sensed in the brain of the user 42, which lowers blood pressure accordingly as part of a physiological feedback loop. The brain is thus "tricked" into playing a more involved interventional role. In some embodiments, one vibration element 136 may be configured to vibrate within a lower frequency range (e.g., 20 kHz to 100 kHz) while the other vibration element 138 may be configured to vibrate at a higher (ultrasound) frequency range (e.g., 100 kHz to 700 kHz), in order to induce multiple types of effect. In other embodiments two or more vibration elements 136, 138 may be configured to vibrate within a lower frequency range while two or more additional vibration elements 136, 138 may be configured to vibrate within a higher frequency range. In some embodiments, one or more vibration elements 136, 138 may be configured to vibrate at multiple frequencies, for example a fundamental frequency (or first harmonic) and a second harmonic. The first harmonic, for example, in a particular embodiment may be 150 kHz and the second harmonic may be 300 kHz. In other embodiments, a third harmonic, or even fourth, fifth, or higher harmonics may be used, as described by the harmonic series. One particular treatment protocol may comprise a first period of activation of the vibration elements 136, 138 which is initiated immediately after the sensing elements 132, 134 detect a change (e.g., increase) in blood pressure. This first period of activation may be followed by pressurization of the cuff 122. In relation to the wearable blood pressure control system 10 of FIGS. 1-8, a further embodiment may add the vibration elements 136, 138. A particular treatment protocol associated with this alternative embodiment may comprise a first period of activation of the vibration elements 136, 138 which is initiated immediately after the sensor 28 detects a change (e.g., increase) in blood pressure. This first period of activation may be followed by an increase in pressurization of the inflatable cuff 22. Though the median nerve 43 is often the target, in other cases, the effect may be focused, or shared, on the radial nerve or the ulnar nerve.

Returning to FIG. 9, in some embodiments, the sensing elements 132, 134 and vibration elements 136, 138 may be replaced by multi-purpose elements which are configured to perform both the sensing function of the sensing elements 132, 134 and the energy application function of the vibration elements 136, 138.

One or more of the sensing elements 132, 134 or vibration elements 136, 138 may be carried on an outer surface 140 of the cuff 122, or may be carried on an inner surface 142 of the cuff 122, or a combination thereof. The cuff 122 is configured to maintain the sensing elements 132, 134 and vibration elements 136, 138 in proximity to the wrist 38 of the user 42 (or other portion of any limb upon which the band 104 has been attached). It may be desired to cover the wrist 38 with an acoustic coupling gel, or other acoustic coupling media, for optimal acoustic coupling between skin of the user 42 and the sensing elements 132, 134 or vibration elements 136, 138. The sensing elements 132, 134 and vibration elements 136, 138 can be secured to the outer surface 140 and/or inner surface 142 of the cuff 122 by an epoxy or adhesive 144 that has appropriate transition acoustic impedance properties. The wearable blood pressure control system 100 also includes a controller 151 and a connection port 191, which will be described in greater detail in subsequent embodiments herein.

Figure 10:
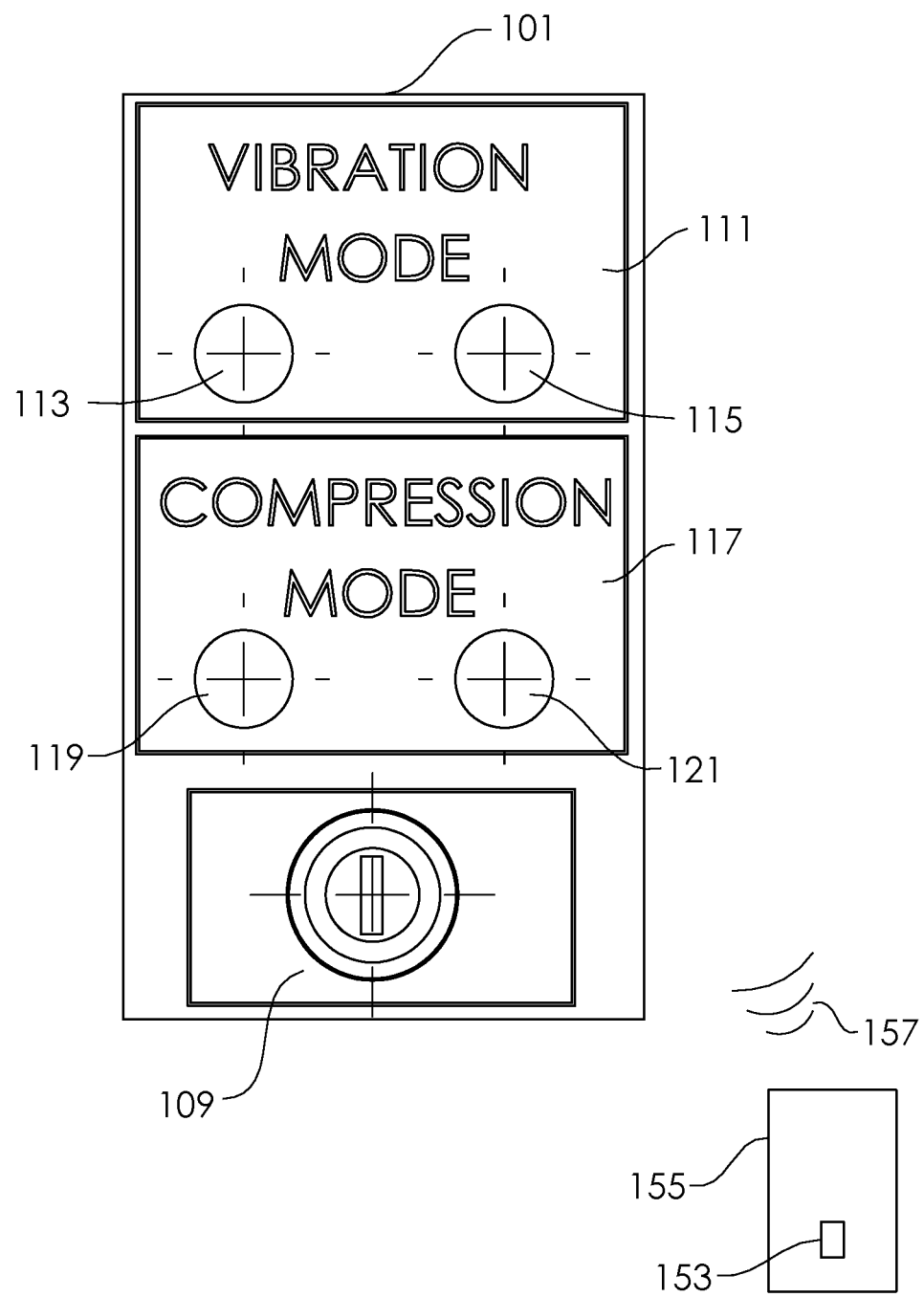
FIG. 10 is a plan view of a user interface of the wearable blood pressure control system of FIG. 9.

FIG. 10 illustrates the user interface 101 which includes a power switch 109 configured for turning the wearable blood pressure control system 100 on or off. The user interface 101 may comprise a touch screen, and may utilize capacitive or resistive touch sensitivity. Alternatively, mechanical or membrane buttons/switches may be utilized. A first control 111 having a first button 113 and a second button 115 is configured for manually adjusting the vibration mode. In other words, the vibration elements 136, 138 may be manually set (for example, to low (intensity) vibration, medium vibration, or high vibration) using the first and/or second buttons 113, 115. One of the buttons 113, 115 may increase the intensity of vibration, while the other button 113, 115 may decrease the intensity of vibration. Alternatively, an application (App) 153 on a mobile phone or device 155 may be configured (via software or firmware) to receive one or more signals 157 from the sensing elements 132, 134, and to automatically adjust the vibration mode, either turning it on or off, or adjusting it between low, medium, and high vibration. The vibration mode in some embodiments may be automatically adjustable, via servo control or other methods, such that the vibration elements 136, 138 are caused to activate in a manner which is proportional to or matches in some way the reduction or increase in amplitude, intensity and/or prevalence of blood pressure changes. For example, the vibration elements 136, 138 may be configured to operate at a derived function of the blood pressure increase that is measured or calculated by the sensing elements 132, 134 (or by the cuff 122 if used as a sphygmomanometer cuff).

A second control 117 having a first button 119 and a second button 121 is configured for manually adjusting the compression mode. The inflation of the interior space 130 of the cuff 122 may be manually set (for example, to low inflation, medium inflation, or high inflation) using the first and/or second buttons 119, 121. One of the buttons 119, 121 may increase the pressure or injected volume of inflation, while the other button 119, 121 may decrease the pressure or injected volume of inflation. Alternatively, the controller 151 within the housing 102 and/or the App 153 may be configured (via software or firmware) to receive one or more signals from the sensing elements 132, 134, and to automatically adjust the compression mode, either turning it on or off, or adjusting it between low, medium, and high compression.

Figure 11:
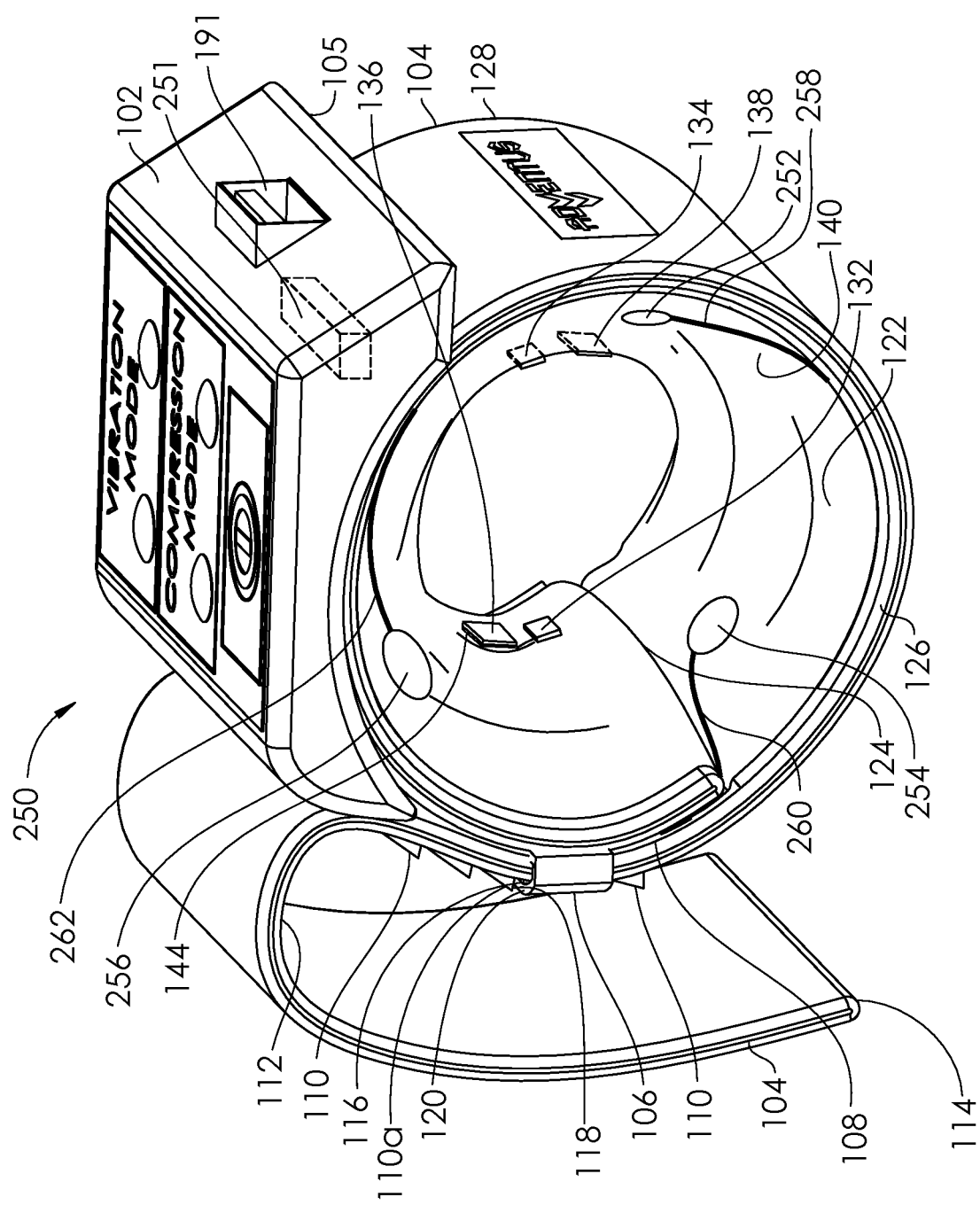
FIG. 11 is a perspective view of a wearable blood pressure control system, according to an embodiment of the present disclosure.

FIG. 11 illustrates a wearable blood pressure control system 250 that is similar to the wearable blood pressure control system 100 of FIG. 9, but additionally comprises stimulation electrodes 252, 254, 256 carried on the outer surface 140 of the cuff 122. The user interface 101 and/or App 153 may be configured to adjust or program a controller 251 such that signals received from the one or more signals from the sensing elements 132, 134 cause current to run through wires or traces 258, 260, 262 electrically coupled to the electrodes 252, 254, 256, thus applying one or more potentials (voltages) across two or more of the electrodes. A current may be applied using voltage control. A current may also be applied using current control. The applied current is capable of activating nerves, such as the median nerve 43, for example, to provide an additional input to the brain of the patient. The user interface 101 (FIG. 10) may include a third mode that is an electrical stimulation mode, also capable of being adjusted manually, or with feedback from the sensing elements 132, 134. Any combination of two or three (or more) modes may be possible, or in some embodiments, only a single mode. The electrodes 252, 254, 256 may be configured such that the one or more applied potentials are directed to the median nerve 43 to thereby stimulate it in order to alter or induce the brain's control or modification of blood pressure. In alternative embodiments, the electrodes 252, 254, 256 may be configured to sense physiological signals related to changes in blood pressure or other cardiovascular parameters.

The controller 251 may be configured or programmable to be configured, via hardware, firmware, or software, such that any one or more of the inflation of the cuff 122, activation of the electrodes 252, 254, 256, or activation of the vibration elements 136, 138 is applied with a particular range of set parameters or set parameter ranges, thus serving as a programmable pulse generator. For example, in certain embodiments, the voltage, current, frequency, or pulse width of the activation of the electrodes 252, 254, 256 may be controlled within the following ranges. Current: 0.1 mA to 200 mA, or 0.1 mA to 50 mA; frequency/rate of application: 0.1 mA to 200 mA, or 1 Hz to 5,000 Hz, or 1 Hz to 1,000 Hz, or 1 Hz to 200 Hz; pulse width: 0.01 microsecond (µs) to 1000 microseconds (µs), or 1 microsecond (µs) to 1000 microseconds (µs), or 0.01 microsecond (µs) to 5 microseconds (µs). The controller 251 may fire the electrodes in a continuous mode, or in random mode comprising one or more bursts. The on-time of the bursts and the off-time of the bursts may each be independently controlled. A particular program or algorithm may be used to vary the on-times and off-times. In alternative embodiments, the controller 251 may be configured or programmable to be configured, via hardware, firmware, or software, such that any one or more of the inflation of the cuff 122, activation of the electrodes 252, 254, 256, or activation of the vibration elements 136, 138 is applied in an at least partially random or pseudo-random manner. The human body is adaptable, and many physiological systems tend to adjust to therapeutic treatments, sometimes in a manner that, to the body, appears helpful, when in fact it is antagonistic to the purposes or effects of treatment. Nervous systems are able to continually change by processes such as synaptic adaptation. Adding in random changes to the way the therapeutic elements (cuff 122; vibration elements 136, 138; electrodes 252, 254, 256) are applied can serve as a way of getting ahead of or "tricking" the body's adaptation schemes that may otherwise actually prove antagonistic to efforts to control blood pressure. Parameters that may be adjusted, randomly, or non-randomly, by the controller 251 include: time of application of energy (mechanical, electrical, etc.), length of interval of time between application of energy, number of repetitions of application of energy, particular operational frequency of a non-static mode of energy (e.g., applying ultrasound at varying pulse rates), amplitude of the applied energy, timing of particular combinations of more than one element of a particular type of energy, or of two or more different types of energy. Any of these parameters can be increased or decreased. The controller 251 may be configured to allow the user/patient to control some or all of these parameter adjustments, for example, via the user interface 101 and/or App 153. In addition, in some embodiments, there may be security levels to control how much the user can control: a first level for a user and a second level for a prescribing physician. In some embodiments, the existence of controls available to the physician that are not available to the user may assure a certain amount of randomness in the treatment. This may even be necessary in some cases, for example, for particular patients that do not want to be surprised with a compression, electrode firing, or vibration event. The security levels may include encryption and/or password control. The "smart" nature of the wearable blood pressure control system 250, or any of the other systems described in the embodiments herein, allows it to be managed by primary care physicians, ad thus, not requiring a specialist. Also, because the device requires no surgery or invasive procedure, only a single healthcare person/location need be involved with the patient's care.

Figure 12:
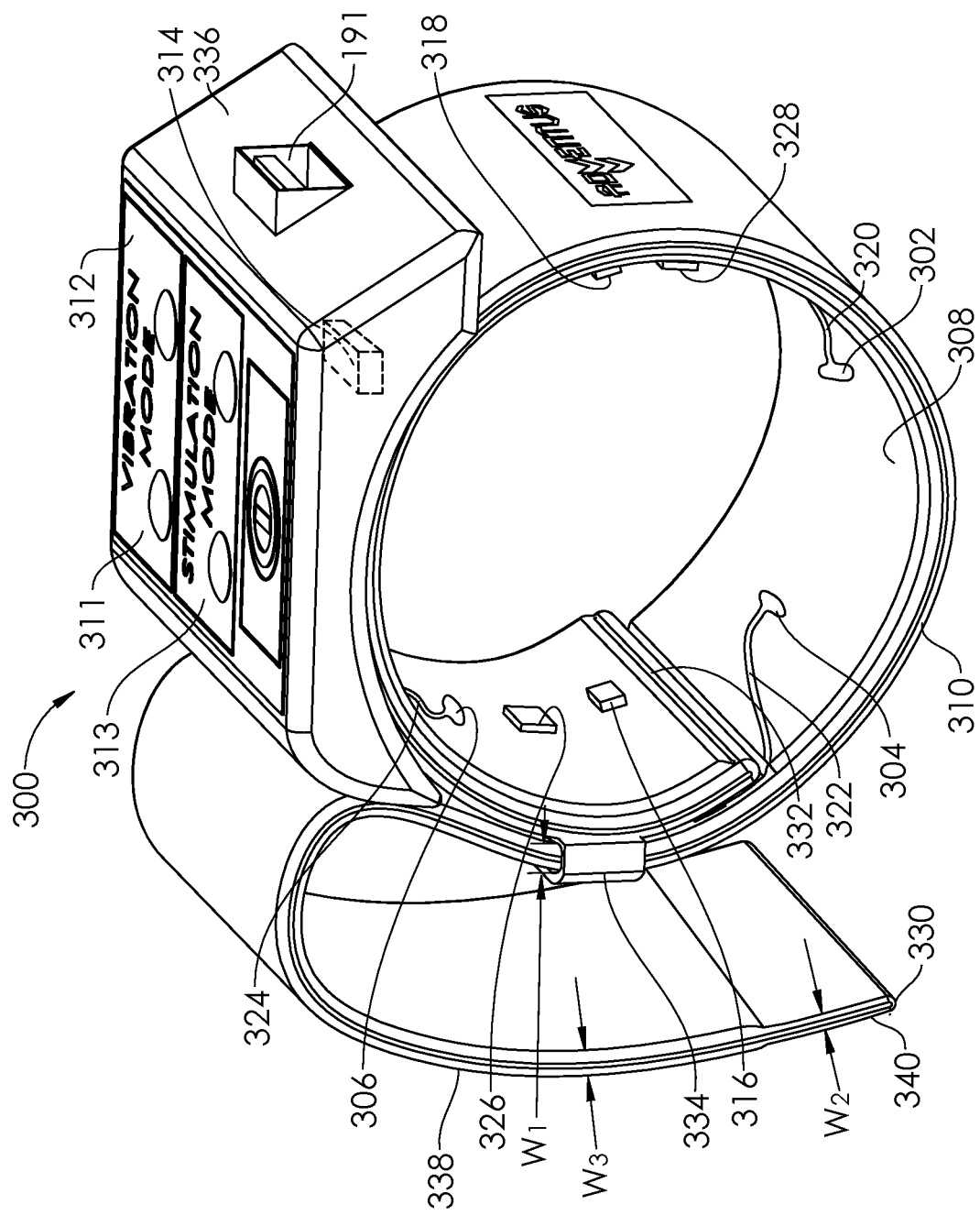
FIG. 12 is a perspective view of a wearable blood pressure control system, according to an embodiment of the present disclosure.

FIG. 12 illustrates a wearable blood pressure control system 300 having multi-mode energy delivery therapy including both vibration and electrical stimulation. The wearable blood pressure control system 300 is similar to the wearable blood pressure control system 100 of FIG. 9, but does not include compression, and does comprise stimulation electrodes 302, 304, 306 carried on the limb-facing surface 308 of the band 310. The band 310 has a first end 330 and a second end 332 and is removably attached to a removable/replaceable housing 336. A loop 334 is secured to the band 310, and has an opening width $W_1$. An insertion section 340 of the band 310 has a thickness $W_2$ that is less than opening width $W_1$. The normal wall 338 of the band 310 has a thickness $W_3$ that is slightly greater than the opening width $W_1$, thus creating a friction fit, which renders wedges 110 or hook/loop 20a/20b unnecessary. In use, a user inserts the insertion section 340 into the loop 334 and pulls the band 310 from the first end 330 until adjusted to an acceptable amount on the limb of the wearer. The friction between the normal wall 338 and the loop 334 maintains the band 310 secure. The user interface 312 and/or App 153 may be configured to adjust or program the controller 314 such that signals sent by the controller in response to one or more signals from the sensing elements 316, 318 cause current to run through wires or traces 320, 322, 324 electrically coupled to the electrodes 302, 304, 306, thus applying one or more potentials (voltages) across two or more of the electrodes. A current may be applied using voltage control. A current may also be applied using current control. The applied current is capable of activating nerves, such as the median nerve 43, for example, to provide an additional input to the brain, which can aid the lowering of blood pressure. The user interface 312 includes a vibration mode 311 and a stimulation mode 313 (via electrode(s)), which are each capable of being adjusted manually, or automatically with feedback from the sensing elements 316, 318. Any combination of the two modes may be possible, such that a mixed signal may be created. The mixed signal may include a cycle having a first period of only one of vibration or stimulation and a second period of the other of vibration or stimulation. The mixed signal may also include at least one period of simultaneous vibration and stimulation. The electrodes 302, 304, 306 may be configured such that the one or more applied potentials are directed to the median nerve 43 to thereby stimulate it in order to alter or induce the brain's control or modification of blood pressure (e.g., lowering blood pressure). In alternative embodiments, the electrodes 302, 304, 306 may be configured to sense physiological signals related to changes in blood pressure or other cardiovascular parameters. The combination of vibration and electrical stimulation working in synchrony can delivery a tailored, optimal result, and can be further informed by the measurement of cardiovascular parameters such as continuous blood pressure, heart rate, heart rate variability, or ECG, including the detection of particular heart arrythmias.

The controller 314 may be configured or programmable to be configured, via hardware, firmware, or software, such that any one or more of the activation of the electrodes 302, 304, 306 or activation of the vibration elements 326, 328 is applied with a particular range of set parameters or set parameter ranges, thus serving as a programmable pulse generator. For example, in certain embodiments, the voltage, current, frequency, or pulse width of the activation of the electrodes 302, 304, 306 may be controlled within the following ranges. Current: 0.1 mA to 200 mA, or 0.1 mA to 50 mA; frequency/rate of application: 0.01 Hz to 50 kHz, or 1 Hz to 5,000 Hz, or 1 Hz to 1,000 Hz, or 1 Hz to 200 Hz; pulse width: 1 microsecond (μs) to 1000 milliseconds (μs), or 1 microsecond (μs) to 1000 microseconds (μs), or 0.01 millisecond (ms) to 5 milliseconds (ms). The controller 314 may fire the electrodes in a continuous mode, or in random mode comprising one or more bursts. The activation may comprise a particular initiation time (start time), a particular end time (stop time), and/or a particular duration. The period of activation of the electrodes 302, 304, 306 may include one or more of the following patterns: a biphasic sine wave, a multiphasic wave, a monophasic sine wave, a biphasic pulsatile sine wave, a biphasic rectangular wave, a monophasic square wave, a monophasic pulsatile rectangular wave, a biphasic spiked wave, a monophasic spiked wave, and a monophasic pulsatile spiked wave. The one-time of the bursts and the off-time of the bursts may each be independently controlled. A particular program or algorithm may be used to vary the on-times and off-times. In alternative embodiments, the controller 314 may be configured or programmable to be configured, via hardware, firmware, or software, such that any one or more of the activation of the electrodes 302, 304, 306 or activation of the vibration elements 326, 328 is applied in an at least partially random or pseudo-random manner, as described in relation for the embodiment of FIG. 11. Any one of the electrodes 302, 304, 306 may serve as a patient return electrode, thus making unnecessary an additional skin-placed return electrode patch. Thus, the simple coupling of the band 310 on the limb of the wearer/user allows the wearer/user to immediately begin using the wearable blood pressure control system 300.

Multiple touch points are provided by the electrodes 302, 304, 306 and vibration elements 326, 328, which are located at different clock locations around the limb-facing surface 308 of the band 310, thus allowing for a high success rate, as an optimal anatomical location for effective therapy is more likely to be identified and treated. The controller 314 may be configured to allow the user/patient to control some or all of these parameter adjustments, for example, via the user interface 312 and/or App 153. In addition, in some embodiments, there may be security levels to control how much the user can control: a first level for a user and a second level for a prescribing physician. In some embodiments, the existence of controls available to the physician that are not available to the user may assure a certain amount of randomness in the treatment. This may even be necessary in some cases, for example, for particular patients that do not want to be surprised with an electrode firing, or vibration event. The security levels may include encryption and/or password control. A connection port 191 may be used to temporarily or permanently attach a USB cable, USB drive, or other cables or drives, for transferring information, charging internal batteries, or supplying power to any internal components. Many of the components described in the wearable blood pressure control system 300 have relatively low power requirements, thus being amenable to a chargeable battery system. The connection port 191 may also be used to attached a wireless antenna, if needed, whether or not there is internal wireless capability within the wearable blood pressure control system 300. The communication can allow the wearable blood pressure control system 300 to be controlled by an application on a mobile device, such as a mobile telephone/smartphone. Data monitoring and analysis can also be done remotely at one or more sites.

The wearable blood pressure control system 300 may include adaptive capabilities. For example, the controller 314 may be programmable, or pre-programmed, to provide a particular therapy plan, such as a morning application of energy, a mid-day application of energy, and an evening application of energy. However, by analyzing changes in one or more cardiovascular parameters measured by the sensing elements 316, 318, the controller 314 may be configured to change the therapy plan to optimize patient response. For example, the change may include a larger amplitude and/or longer duration of the application of vibrational energy and a smaller amplitude and/or shorter duration of the application of electrical stimulation energy. Or, in other cases, the change may include a larger amplitude and/or longer duration of the application of electrical stimulation energy and a smaller amplitude and/or shorter duration of the application of vibrational energy. An energy modulation algorithm may be applied, to allow the wearable blood pressure control system 300 to learn to better deliver custom neuromodulation management to each wearer, which may correspond to each patient's blood pressure or other cardiovascular parameter. The wearable blood pressure control system 300 is thus able to learn from the physiology and treatment effect of each patient for a personalized and optimized treatment. Each individual energy modality (application of electrical stimulation or application of vibration) can be optimized, and the combination of more than one energy modality can also be optimized. Beat-to-beat intervals used in the calculation of heart rate or heart rate variability may be derived from ECG data or from blood pressure data. In some embodiments, an RR interval (from successive R points in the QRS complex of the ECG) is used. RR Intervals are sometimes called NN intervals when referring to an RR interval in a normal beat of the heart, or more particularly, beats of the heart not including beats not originating in the sinoatrial node. In some embodiments, time-domain methods may be used for beat-related calculations. In other embodiments, geometric methods may be used for beat-related calculations. In other embodiments, frequency domain methods may be used for beat-related calculations.

Figure 13:
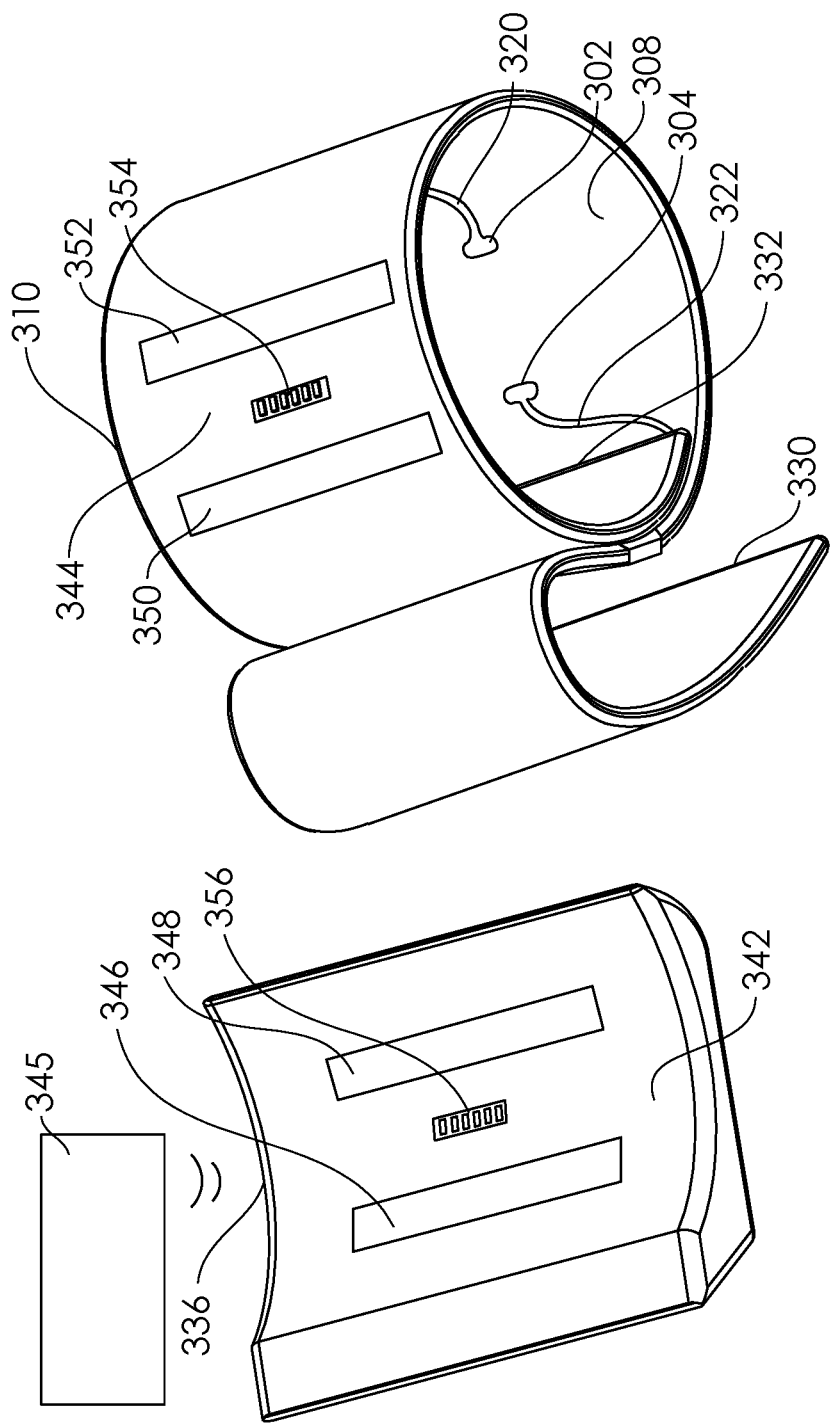
FIG. 13 is a perspective view of the wearable blood pressure control system of FIG. 12 in a decoupled state.

In FIG. 13, the housing 336 has been removed from the band 310. The housing 336 is removeable from and reattachable to the band 310 for multiple reasons. The housing 336 may include one or more rechargeable batteries which can be recharged by attachment of a power cable to the connection port 191, or to another port, connected to the batteries. The batteries may be rechargeable by wired or by wireless methods, including inductively-coupled charging. A wireless charging unit 345 may also be used to charge the batteries. In alternative embodiments, one or more of the batteries may be a primary cell, configured to be used and discarded (or recycled). The housing 336 is secured to the band 310 via two magnets 346, 348 which are configured to attract magnets 350, 352 carried on a surface 344 of the band 310. In the embodiment of FIG. 13, magnet 348 has an externally-facing positive pole which is configured to magnetically engage with magnet 350, which has an externally-facing negative pole. Magnet 346 has an externally-facing negative pole which is configured to magnetically engage with magnet 352, which has an externally-facing positive pole. The magnets may comprise rare earth magnets, such as neodymium-iron-boron or samarium cobalt. The neodymium-iron-boron magnets may be chosen from a grade of N30 or higher, or N33 or higher, or N35 or higher, or N38 or higher, or N40 or higher, or N42 or higher, or N45 or higher, or N48 or higher, or N50 or higher. In some embodiments, the neodymium-iron-boron magnets may have a grade between N30 and N52, or between N33 and N50 or between N35 and N48. In some embodiments one of the two magnets in each attractive pair may be replaced by a magnetic material such as iron, or 400-series stainless steel, which can be attracted by a pole of the opposing magnet.

Electrical connection may be achieved by conductive projections 354 carried on the band 310 and which are configured to conductively engage with conductive depressions 356 carried on the bottom surface 342 of the housing 336. The conductive depressions 356 are electrically connected to the various electrical components of the housing 336, which may include the user interface 312, the controller 314, and the connection port 191. The conductive projections 354 are electrically connected to the traces 320, 322, 324 and stimulation electrodes 302, 304, 306, the vibration elements 326, 328, and the sensing elements 316, 318 (FIG. 12). Thus, when the housing 336 is attached to the band 310 via the attraction of the magnets 346, 348, 350, 352, the conductive projections 354 are electrically coupled to the conductive depressions 356. The user interface 312, the controller 314, and the connection port 191 are thereby electrically interlinked with the traces 320, 322, 324 and stimulation electrodes 302, 304, 306, the vibration elements 326, 328, and the sensing elements 316, 318. A user may choose to remove the housing 336 from the band 310 for other reasons than recharging. For example, a first housing 336 may be replaced by a second housing 336, if the first housing 336 is damaged or ceases to function. The housing 336 may be removed to present to a medical facility, which may upload or download information or software revisions, or for maintenance or repair. The conductive projections 354 and the conductive depressions 356 are shown in FIG. 13 between the magnets 350, 352 or magnets 346, 348, respectively, but in other embodiments, the conductive projections 354 and/or the conductive depressions 356 may be located laterally from the magnets 350, 352 and/or magnets 346, 348. In some embodiments, the conductive projections 354 and conductive depressions 356 may each be replaced by a series of conductive terminals that each have both projections and depressions, or by a series of terminals that have a substantially planar array of conductive terminals (neither projections nor depressions).

In alternative embodiments, the magnets 346, 348, 350, 352 may be substituted by other connections, such as snaps, hooks-and-loops (Velcro®), sliding engagements, or adhesive strips.

Figure 14:
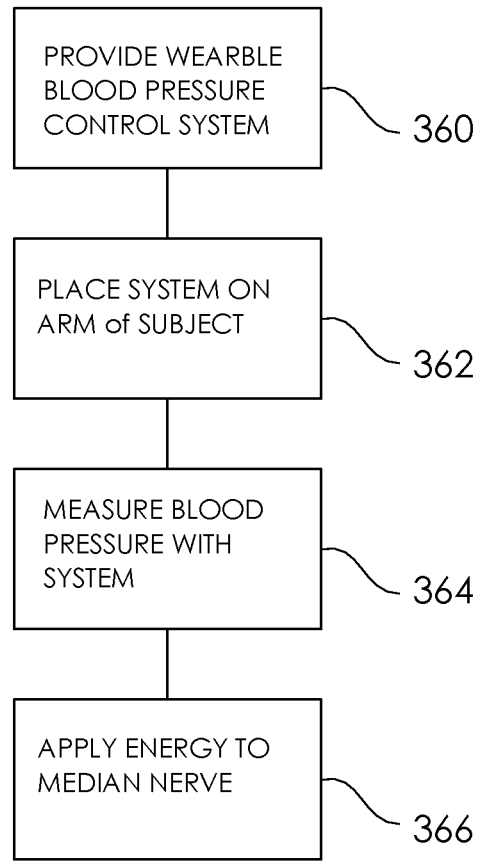
FIG. 14 is a flow chart describing a method for controlling blood pressure in a subject.

A method for controlling blood pressure in a subject is described in relation to FIG. 14. In a first step 360 a wearable blood pressure control system 10, 100, 250, 300 is provided. In a second step 362, the wearable blood pressure control system 10, 100, 250, 300 is placed on an arm of the subject. The wearable blood pressure control system 10, 100, 250, 300 may be placed in proximity to the median nerve 43. In some cases, the wearable blood pressure control system 10, 100, 250, 300 may be placed on the right arm in proximity to the right median nerve. In some cases, the wearable blood pressure control system 10, 100, 250, 300 may be placed on the left arm in proximity to the left median nerve. In some cases, a first wearable blood pressure control system 10, 100, 250, 300 may be placed on the right arm in proximity to the right median nerve and a second wearable blood pressure control system 10, 100, 250, 300 may be placed on the left arm in proximity to the left median nerve.

In a third step 364, the wearable blood pressure control system 10, 100, 250, 300 measures blood pressure of the subject. The blood pressure may in some cases be measured via a sphygmomanometer cuff, and in other cases, the blood pressure may be measured by a blood pressure sensor. In some cases, a sensor and a sphygmomanometer cuff may work in conjunction with each other to measure blood pressure. The blood pressure measured may be presented or analyzed as a systolic pressure over a diastolic pressure, or in other cases may be presented or analyzed as a mean arterial pressure (MAP). In a fourth step 366, if the blood pressure is determined to be elevated, or high, or hypertensive, or above a predetermined threshold, the wearable blood pressure control system 10, 100, 250, 300 applies energy to the median nerve of the arm on which the wearable blood pressure control system 10, 100, 250, 300 is worn. The energy applied may comprise compressive stresses (pressure), or electrical stimulation, or vibratory stimulation, ultrasonic stimulation, or heat application, or heat removal (cooling), or magnetic exposure, or electromagnetic exposure, or sonic stimulation, or other mechanical energy application. In some cases, the application of energy to the median nerve may have duration of between about five minutes and about one hour, or between about ten minutes and about 45 minutes, or between about 15 minutes and about 35 minutes, or between about 20 minutes and about 30 minutes, between about one minute and ten minutes, or between about five minutes and about ten minutes. The combination of energy application modalities (e.g., vibration and electrical stimulation) can be effective in significantly reducing the time required to reduce blood pressure in the patient. Once the increase blood pressure is sensed, a combination of energy application modalities can lower the blood pressure in less than about fifteen minutes, or less than about ten minutes, which is significantly faster than traditional single energy modalities.

The wearable blood pressure control system 10, 100, 250, 300 may be configured or configured to be programmable so that step 364 (and step 366 if determined by the system to be appropriate) occur at particular periods in the day while the subject wears the wearable blood pressure control system 10, 100, 250, 300. For example, the step(s) may be applied a) when the subject wakes up or gets out of bed, b) at a particular time in the morning (e.g., after eating), c) at a particular time in the middle of the day (e.g., immediately before lunch, during lunch, or immediately after lunch), prior to going to bed or at some other time in the evening. The wearable blood pressure control system 10, 100, 250, 300 may be configured or configurable to perform step 364 one, two, three, or more times per day. The wearable blood pressure control system 10, 100, 250, 300 may be configured or configurable to perform step 366 one, two, three, or more times per day.

Figure 15:
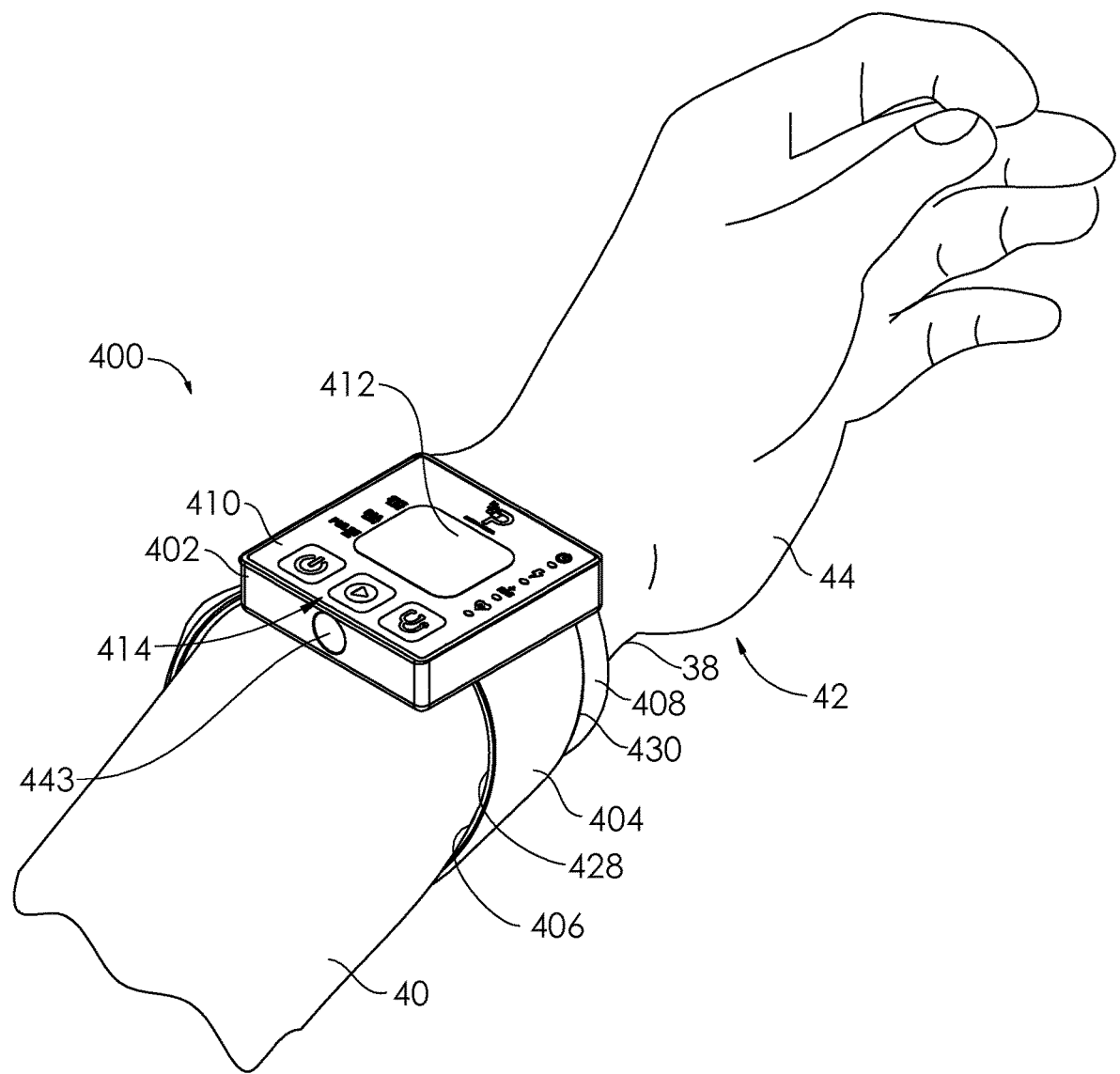
FIG. 15 is a perspective view of a wearable blood pressure control system in use on the wrist of a user, according to an embodiment of the present disclosure.

FIG. 15 illustrates a wearable blood pressure control system 400 having multi-mode energy delivery therapy including both vibration and electrical stimulation. The wearable blood pressure control system 400 includes features of the wearable blood pressure control system 250 of FIG. 11, the wearable blood pressure control system 300 of FIG. 12, and the wearable blood pressure control system 100 of FIG. 9, as well as having other distinct features. A housing 402 is connected to a first band 404 by any of the manners described herein. The first band 404, having a first end 401 and a second end 403, includes an adjustable internal surface 406 which is configured to be inflated to allow the first band 404 to fit onto a wide range of limb sizes (e.g., arm circumference, wrist circumference, etc.). The first band 404 may be secured to itself by a hook and loop system or any of the other modalities described herein in relation to the other embodiments. A second band 408 is carried in parallel with the first band 404 and is configured to place a sensing module and/or an energy application module in proximity to the limb. The sensing module can be configured to measure one or more cardiovascular parameters, including blood pressure, electrocardiographic data, heart rate or, heart rate variability from the limb. The energy application module may be configured to delivery two or more types of energy to the limb, such as vibrational energy or electrical stimulation energy. A user interface 410 having a display 412 and controls 414 is carried on top of the housing 402.

Figure 16:
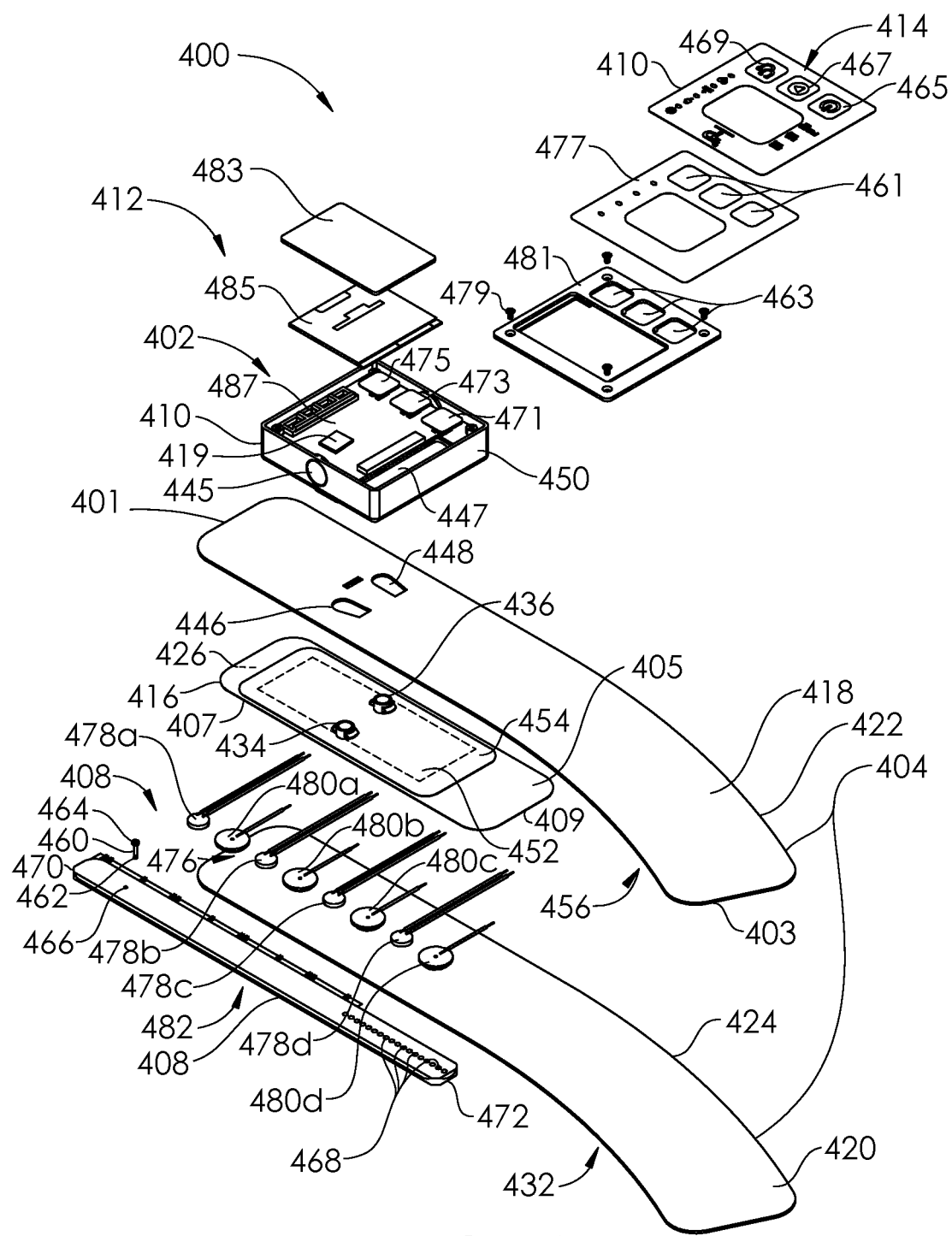
FIG. 16 is an exploded view of the wearable blood pressure control system of FIG. 15.
Figure 17:
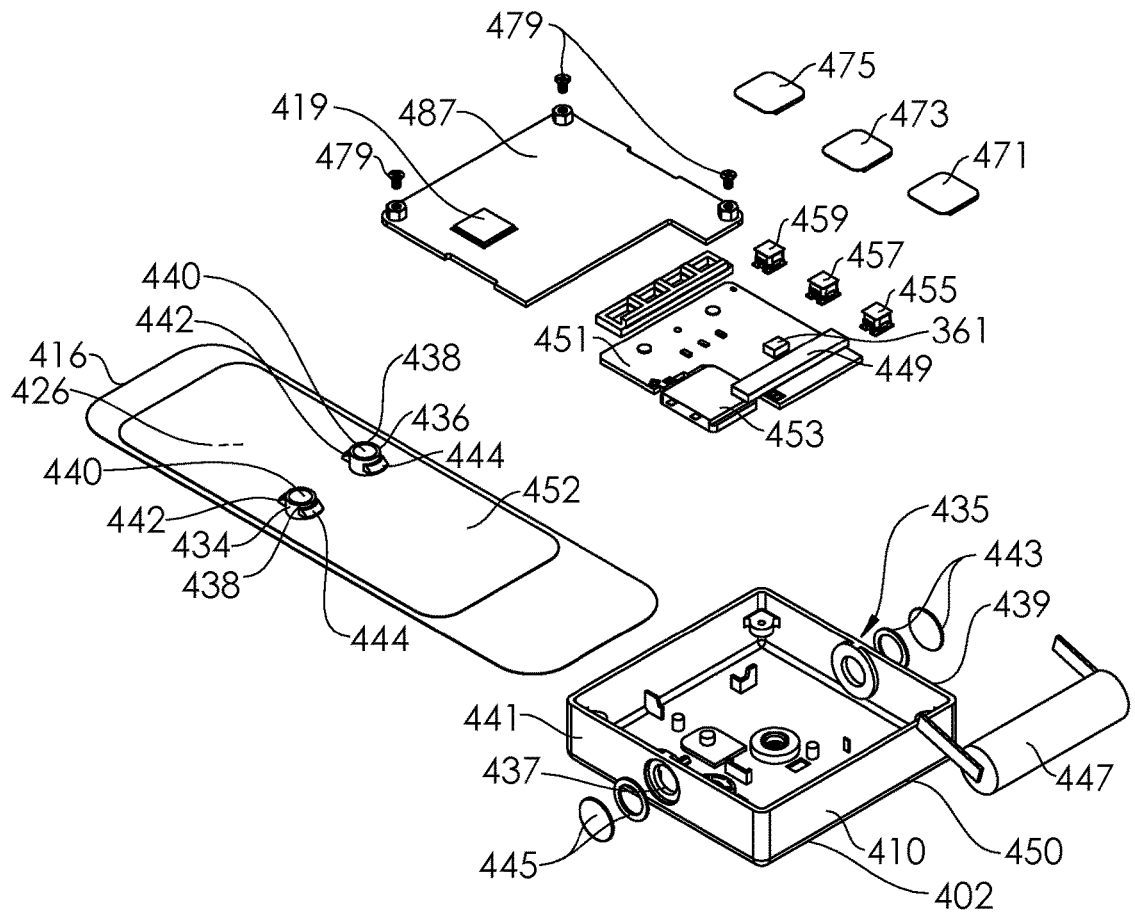
FIG. 17 is a further exploded view of the wearable blood pressure control system of FIG. 15.

The first band 404, shown in detail in FIG. 16, comprises an inflatable bladder 416 which is sealed within an upper band 418 and a lower band 420. The bladder 416 may comprise a relatively high strength, flexible material such as polyurethane or polyethylene terephthalate (PET). The bladder 416 may comprise an upper sheet 405 and a lower sheet 407, sealed around a perimeter seal 409. The upper band 418 and the lower band 420 may comprise a fabric, such as woven polyamide (nylon). The perimeter 422 of the upper band 418 is sealed to the perimeter 424 of the lower band 420, such that when an interior cavity 426 of the bladder 416 is inflated with air, the lower band 420 is forced away in a radial direction from the upper band 418, except at circumferential seams 428, 430 (FIG. 15). Thus, a contact surface 432 of the lower band 420 serves as the adjustable internal surface 406, configured to contact the skin of a limb of a user. The perimeters 422, 424 may be sealed to each other with hot melt adhesive, thermal bonding, or epoxies or adhesives. The bladder 416 includes an inlet port 434 for entry of inflation fluid (e.g., air) and an outlet port 436 for exit of the inflation fluid. Each of the ports 434, 436 has an external diameter 438, an inner diameter 440, and tapered snap wings 442, 444, as shown in FIG. 17. Returning to FIG. 16, the ports 434, 436 extend through holes 446, 448 of the upper band 418, respectively, such that they are accessible for attachment to a main housing 450 of the housing 402. The bladder 416 is trapped (e.g., sandwiched) between the upper band 418 and the lower band 420 without being bonded at the bonding region 454. Thus, the bladder is not over constrained in relation to the upper band 418 or the lower band 420, and the outer surfaces of the bladder 416 are able to slide along the inner surfaces of the upper band 418 and lower band 420 as the bladder 416 is inflated. In an alternative embodiment, the bladder 416 includes an upper face 452 having a bonding region 454, at least around its periphery 458 or a portion of its periphery 458, that is bonded to an underside 456 of the upper band 418. The bonding region 454 may be sealed to the underside 456 of the upper band 418 by hot melt adhesive, thermal bonding, or epoxies or adhesives.

Figure 18:
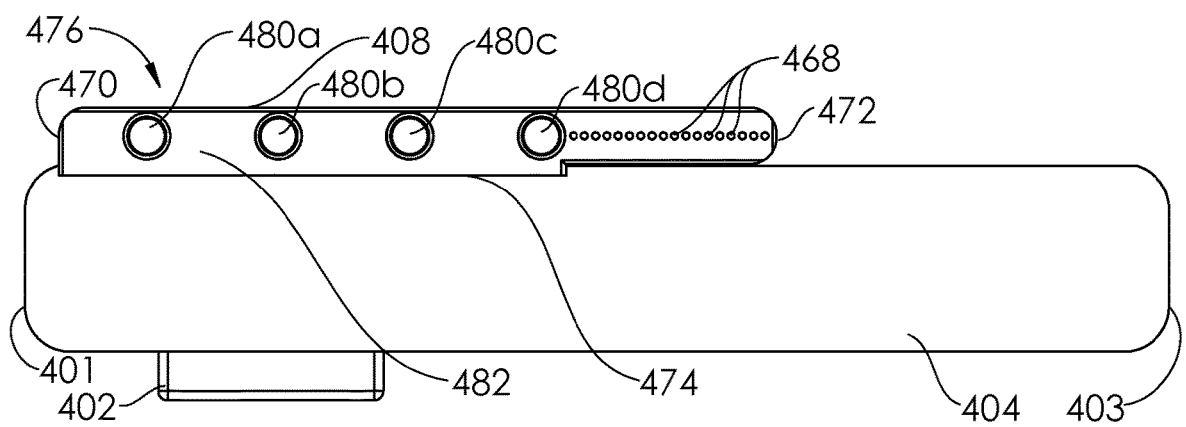
FIG. 18 is a bottom view of the wearable blood pressure control system of FIG. 15.
Figure 19:
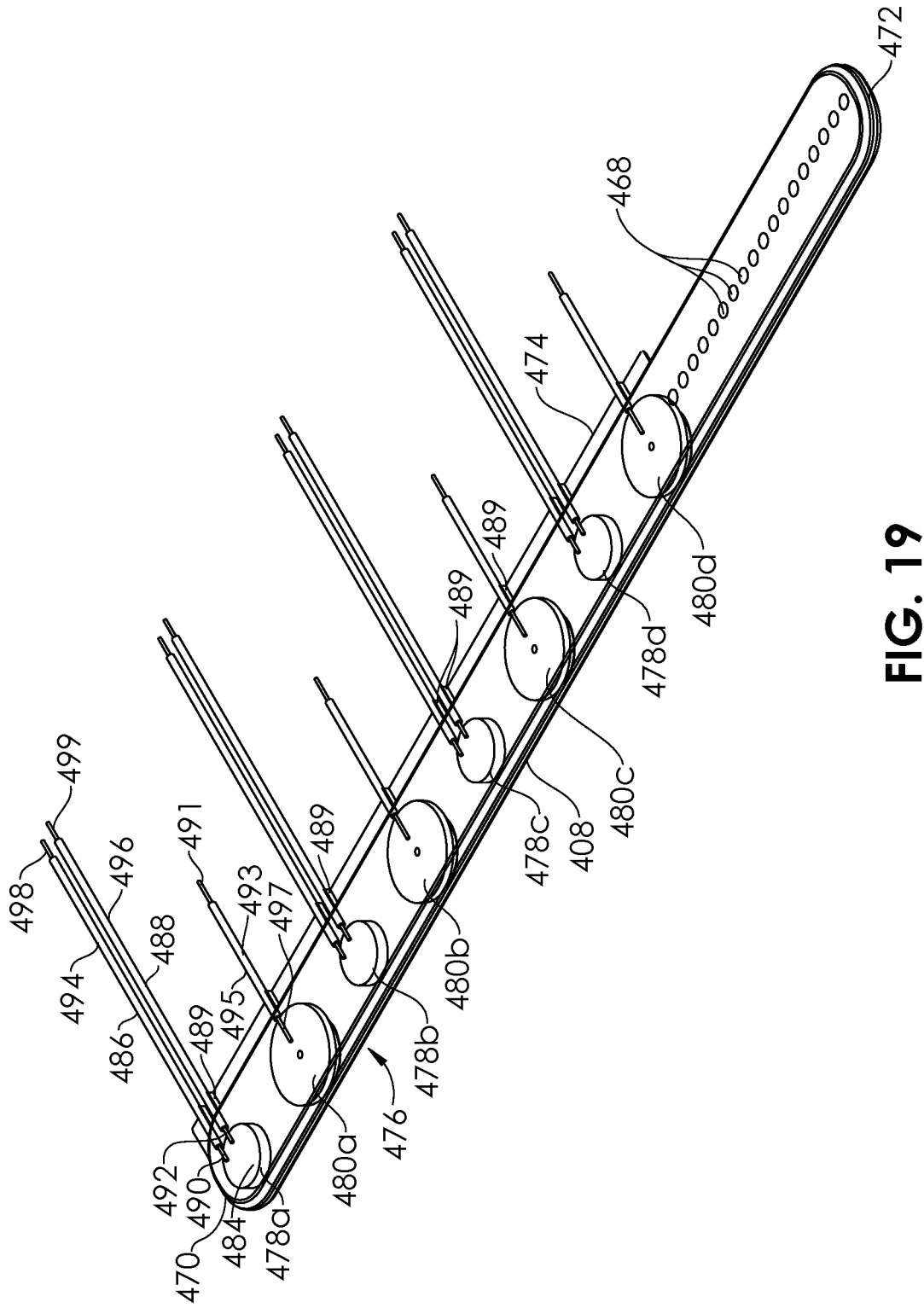
FIG. 19 is a perspective cut-away view of a sensing module of the wearable blood pressure control system of FIG. 15.

An attachment pin 460 has a distal end 462 that is attached into a hole 466 in a first end 470 of the second band 408 and an increased diameter proximal end 464 configured for removably snapping into one of a series of holes 468 in a second end 472 of the second band 408. The second band 408 is secured to the first band 404 along a lateral edge 474, as shown in FIG. 18, such that when the first band 404 and second band 408 are secured around a limb, a series of active elements 476 are coupled in proximity to the skin of the limb. The securement of the second band 408 to the first band 404 may be by stitching, welding, overmolding, or thermal bonding. Returning to FIG. 16, the active elements 476 comprise four ceramic piezoelectric discs 478 (478a-d) and four electrodes 480 (480a-d). The piezoelectric discs 478 may be fully molded within the second band 408. The second band 408 may comprise a material that acoustically couples to the piezoelectric crystals of the piezoelectric discs 478, for example, a silicone elastomer. The electrodes 480 are exposed at a contact surface 482 of the second band 408, as shown in FIG. 18, such that they may directly contact the skin of the user when the second band 408 is secured to the limb of the user. An acoustic coupling gel may be used on the contact surface 482 and on the electrodes 480, to maximize the coupling to the skin of the subject. Turning to FIG. 19, the second band 404 is shown transparently, such that the active elements 476 are visible in their embedded array. Each piezoelectric disc 478a-d has an electrically conductive layer 484 that may be sputtered or applied by other forms of deposition. A first conductor wire 486 and second conductor wire 488 are soldered to the electrically conductive layer 484 at first bare ends 490, 492. The conductor wires 486, 488 may include outer insulative jackets 494, 496 along most of their lengths. Second bare ends 498, 499 of the conductor wires 486, 488 are configured for electrically coupling to electronic components within the housing 402. Each electrode 480a-d is soldered to a bare end 497 of a conductor wire 495 having an insulative jacket 493. A second bare end 491 is configured for electrically coupling to electronic components within the housing 402. The lateral edge 474 of the second band 408 includes a plurality of snaps 489 configured for snapping and securing the insulative jackets 493, 494, 496 of the conductor wires 495, 486, 488, to hold the conductor wires 495, 486, 488 in place in relation to the second band 408 and the first band 404, thus holding them in place and providing strain relief.

Returning to FIG. 16, the main housing 450 includes a main circuit board 487 and a liquid crystal display (LCD) 485, covered by a glass cover 483. These components are enclosed within the main housing 450 by a cover 481, which is secured to the main housing by screws 479. The user interface 410 is adhered to the cover 481 by a shaped adhesive layer 477. Actuatable buttons 475, 473, 471 coupled to the main circuit board 487 are accessible via touch buttons 469, 467, 465 of the user interface 410, and via cutaways 463, 461 in the cover 481 and the adhesive layer 477, respectively. FIG. 17 shows the tactile switches 459, 457, 455 that are actuated by pressing the actuatable buttons 475, 473, 471, respectively. In alternative embodiments, the user interface may include capacitive touch sensitivity or resistive touch sensitivity. A diaphragm pump 453 is carried on an auxiliary circuit board 451, configured for controlling blood pressure measurements. The pump 453 may comprise a piezoelectric-actuated micropump. A spacer 449 is configured to separate the auxiliary circuit board 451 from the main circuit board 487 for space or cooling concerns, but the main circuit board 487 is electrically coupled to the auxiliary circuit board 451. Either of the circuit boards 451, 487 may be fabricated by printing or other mass fabrication techniques. Power is provided to the electronic components by a battery 447, also contained within the housing 402. In some embodiments, the battery comprises a rechargeable battery. In some embodiment, the battery comprises a lithium ion 3.7 Volt rechargeable battery. The main circuit board 487 is configured to transfer power and/or control to the auxiliary circuit board 451. The auxiliary circuit board 451 is configured to use some of this power to drive the pump 453. A microcontroller 419 is carried on the main circuit board 487, but may alternatively be carried on the auxiliary circuit board 451. The microcontroller 419 may be programmed or programmable to control the operations of any of the functions of the wearable blood pressure control system 400. The microcontroller 419 may control parameters such as start time, stop time, rise time, intensity, or any RAM timing parameters (memory timing parameters), such as column address strobe (CAS) latency, row address to column address delay, row pre-charge time, or row active time.

Additional electrodes 445, 443 are carried within circular depressions 437, 435 in sides 441, 439 of the main housing 450, respectively. And are electrically coupled to one or both of the main circuit board 487 or auxiliary circuit board 451. In some embodiments, one or both of the circuit boards 487, 451 may be configured to receive input from the electrodes 480a-d and one or more of the electrodes 445, 443 in order to obtain electrocardiographic data (ECG). In use, a subject places the wearable blood pressure control system 400 onto a first limb, for example, by wrapping the bands 404, 408 around the subject's left wrist, and securing them. The subject then initiates an electrocardiographic measurement via the user interface 410, and then touches either one of the electrodes 445, 443 of the main housing 450 with a finger of the subject's right hand. The electrodes 480a-d, 445 (or electrodes 480a-d, 443, or other combinations) together create multiple ECG vectors to allow for useful cardiovascular data. The incorporation of both the left wrist and the right hand (via at least one finger), provides the bilateral input important for a reliable and physiologically indicative electrocardiogram (ECG). In some embodiments, the touching of the finger to the electrode 445 or electrode 443 automatically initiates the electrocardiographic measurement, without requiring the use of the touch buttons 469, 467, 465 of the user interface 410. In some embodiments, the control circuitry can be configured or programmed such that the touch of one of the electrodes 445, 443 with a finger initiates and maintains ECG measurement, and the removal of that finger stops ECG measurement.

Figure 20A:
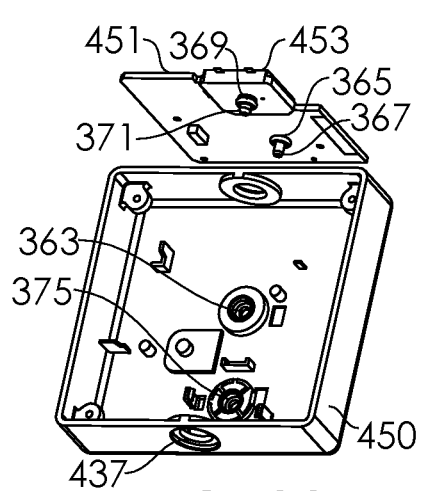
FIG. 20A is a first exploded view of a pump and bladder assembly of the wearable blood pressure control system of FIG. 15.
Figure 20B:
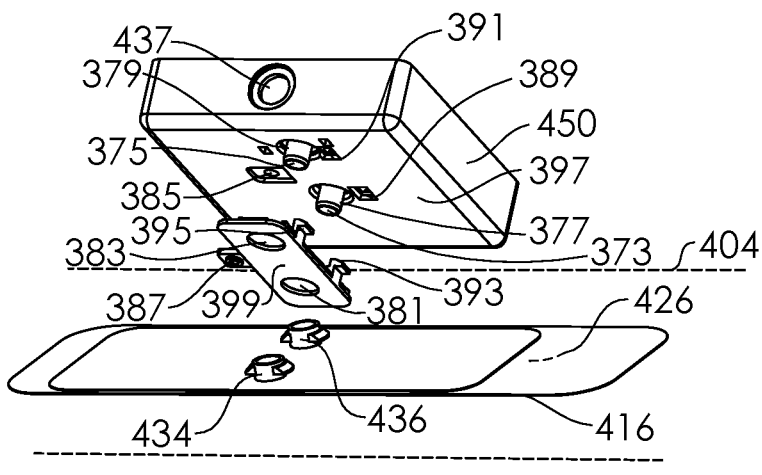
FIG. 20B is a second exploded view of a pump and bladder assembly of the wearable blood pressure control system of FIG. 15.

FIGS. 20A and 20B illustrates the connections between the bladder 416 and the pump 453. The pump 453 includes an outlet port 371 that is secured into inner cylindrical cavity 375 in the main housing 450. An o-ring 369 carried around the outlet port 371 provides a seal between the pump 453 and the main housing 450, as the o-ring 369 seals the communication between the outlet port 371 and the cavity 375. An exhaust port 367, having an o-ring 365 therearound seals into an inner cylindrical cavity 363 in the main housing 450. Thus, air being emptied from the bladder 416 will exit through the auxiliary circuit 451, and into the interior of the housing 402. A solenoid 361 (FIG. 17) carried on the auxiliary circuit 451 may be controlled by the microcontroller 419 to close or open the solenoid 361, to keep air within the bladder 416 or allow air to exit the bladder 416. A snapping bracket 399 is secured to the lower side 397 of the main housing 450 by inserting tabs 395, 393 of the snapping bracket 399 in slots 391, 389 of the main housing 450, respectively, and then tightening a screw (not shown) through a hole 387 in the snapping bracket 399 and into a threaded hole 385 in the lower side 397 of the main housing 450. The ports 434, 436 of the bladder 416 are snapped into the holes 383, 381, respectively, of the snapping bracket 399. The tapered snap wings 442, 444 allow the lead-in of the ports 434, 436 into the holes 383, 381, and secure attachment with the snapping bracket 399 and the main housing 450 (and thus, the housing 402). In some embodiments, the tapers of the tapered snap wings 442, 444 is only on the lead-in side (as shown), and so the bladder 416 can be attached to the housing 402, but not detached. In other embodiment, there may also be tapers on the lower sides of the tapered snap wings 442, 444, and so the bladder 416 can be attached to and detached from the housing 402. The bladder 416 and first band 404 can thus be configured to be disposable and replaceable in some embodiments. In these embodiments, the first band 404 and second band 408 may be removably connectable to each other, for example with snaps, hooks and loops, rib and groove configurations, or adhesive attachment. When the ports 434, 436 are snapped through the holes 383, 381, tapered hubs 379, 377 having the extension of the inner cavities 375, 373 sealingly engage into the inner diameters 440 of the ports 434, 436. This completes the sealing communication between the pump 453 and the bladder 416.

The adjustable internal surface 406 of the first band 404 is configured to automatically inflate to an appropriate size (e.g., by the bladder 416 being inflated by the pump 453 with a particular volume of air) such that it applies the appropriate amount of snugness (radially-applied pressure) to the limb at the site of attachment. The microcontroller 419 can be programmed or programable to initiate a bladder inflation cycle using feedback from any two of the electrodes 480. The electrodes 480 may additionally or alternatively be located on the contact surface 432 of the lower band 420, instead of only on the second band 408. Two electrodes 480 can be configured to measure an impedance of the limb tissue between them. Thus, as the bladder 416 is inflated, the measured impedance makes a sudden change (spike) with the two electrodes 480 each become substantially coupled to the skin. This occurs with the two electrodes 480 each have at least a nominal normal force against the skin. This sudden change in the impedance measurement when an impedance through the limb tissue is being measured, with air no longer an impedance component, can be used by the microcontroller 419 to signal the pump 453 to stop injecting air into the bladder 416. The bladder 416 is now adjusted for the appropriate or desired "fit" of the first band 404. In a band 404 Alternatively, the internal pressure of the bladder 416 may be measured with an internal pressure transducer (not shown). The bladder pressure can be monitored, and the microcontroller 419 will signal pump 453 to stop injecting air into the bladder 416 when a spike in the pressure is detected.

Figure 21:
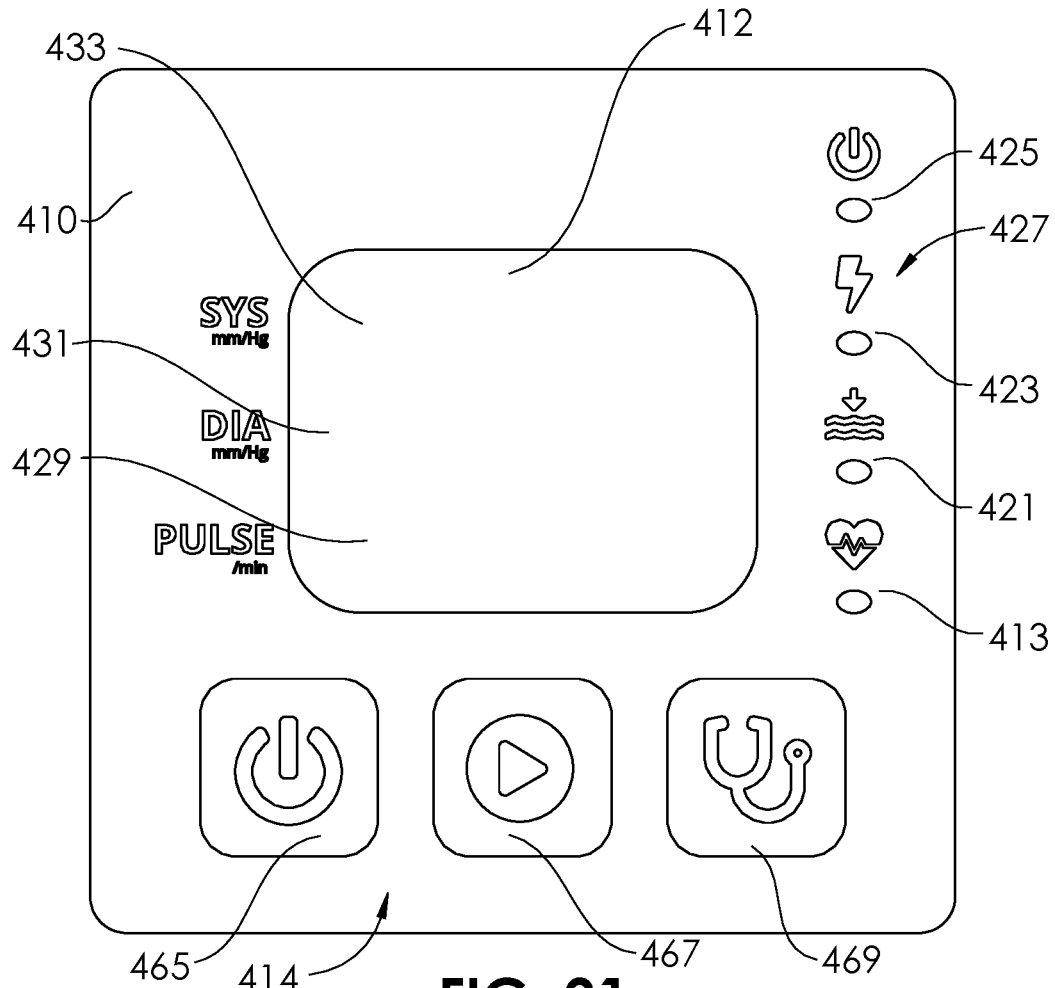
FIG. 21 is a plan view of a user interface of the wearable blood pressure control system of FIG. 15.

The user interface 410 is shown in more detail in FIG. 21. The display 412 includes a first line 433 configured to display a current or latest-measured value of systolic blood pressure, for example, systolic arterial blood pressure. The display 412 includes a second line 431 for a current or latest-measured value of diastolic blood pressure, for example, diastolic arterial blood pressure. Alternatively, in place of these two lines of text 433, 431, a graph of blood pressure may be displayed, with time in the x-axis and pressure in the y-axis. In other embodiments, the two lines of text 433, 431 may be replaced by a single line (or may be augmented by an additional line) showing a current or latest-measured value for mean pressure, for example mean arterial pressure (MAP). The blood pressure may be displayed, whether a value or a graph, by units of mm Hg, or by other units. The display 412 includes a third line 429 for a current or latest-measured value of pulse or heart rate, e.g., beats per minute. A secondary or alternative display location on the display 412 may indicate heart rate variability.

Controls 414 in FIG. 21 are assigned to: an on/off button 465 by which a user turns the user interface 410 on or off; a start/stop button 467, by which a user stops or starts a program of treatment application, with or without automatic intermittent blood pressure measurement (depending on programmed status); and a blood pressure measurement button 469, by which a user initiates a blood pressure measurement cycle. Alternatively, the button 469 can be configured to initiate a pulse (heat rate) measurement cycle. Though not shown, an additional button may be configured to notify emergency medical personnel. Alternatively, the holding down of one of more of the controls 414 may achieve this task. The wearable blood pressure control system 400 may be configured to communicate with a mobile phone or other mobile device to make the call to an emergency system, or to a preprogrammed medical professional. Indicator lights 427, which may comprise LEDs, include: an on/off status indicator 425; an indicator of active status of applied electrical stimulation 423; an indicator of active status of applied vibration/ultrasound 421; and an ECG indicator 413, which indicates when ECG is being measured. In other embodiments, the ECG indicator 413 may alternatively be configured to indicate when electrodes are not sufficiently coupling to skin, or may even indicate when the measured ECG is critical or indicates arrythmias in the subject. Any additional indicator lights 427 may be added to achieve these or other functions.

Figure 22:
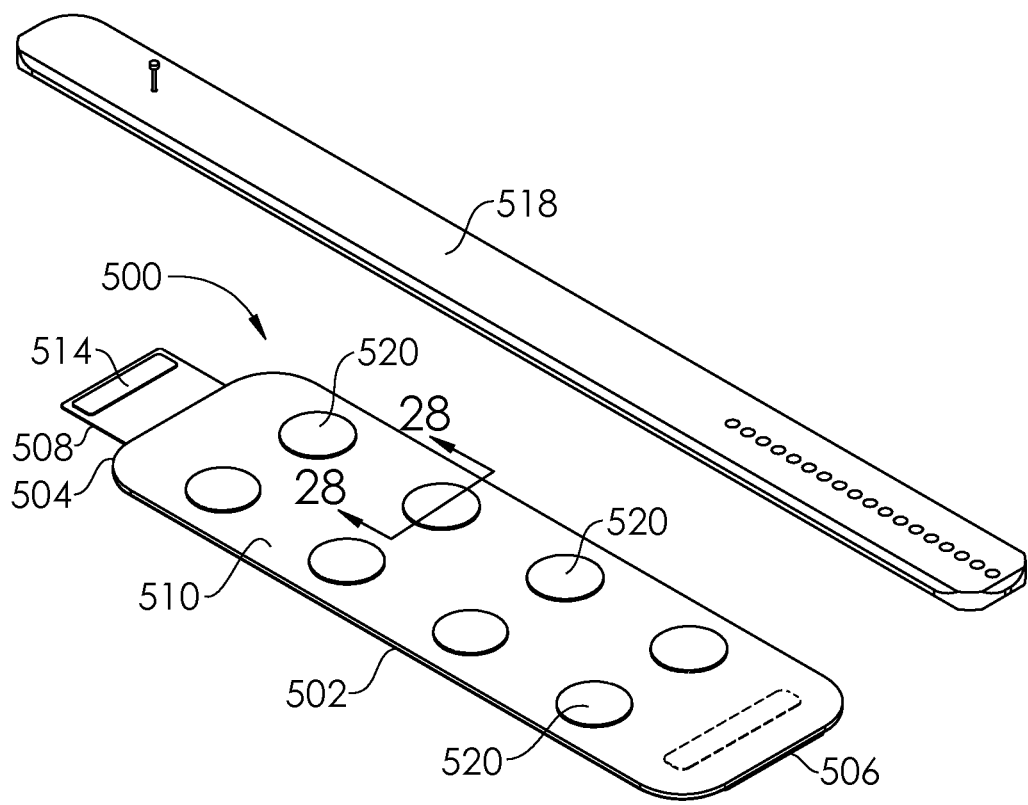
FIG. 22 is a perspective view of a wearable blood pressure control system, according to an embodiment of the present disclosure.
Figure 25:
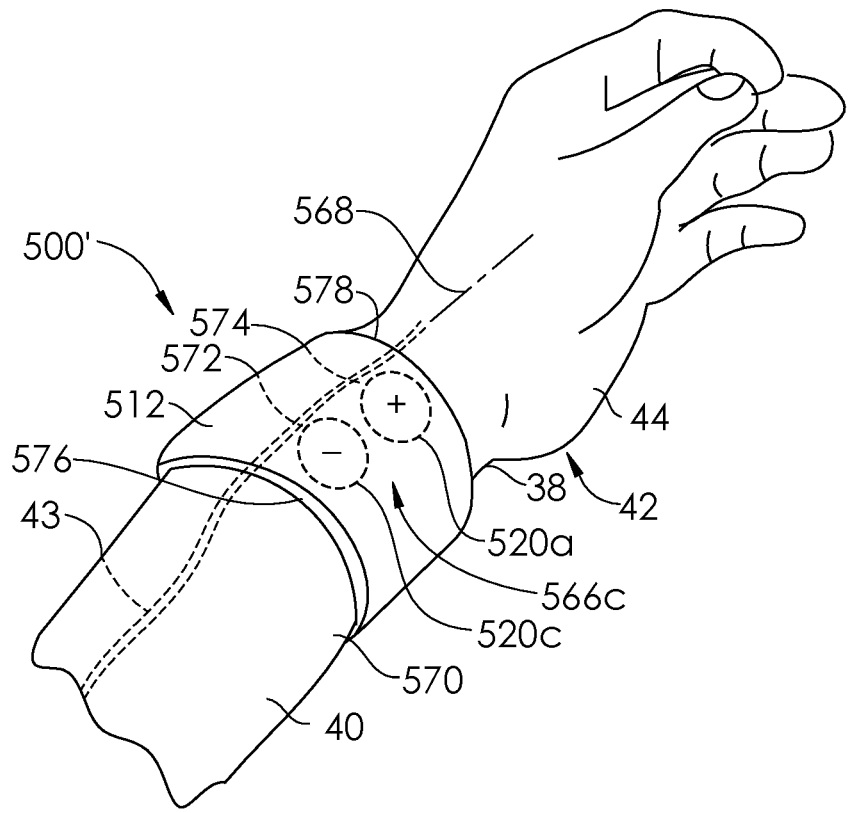
FIG. 25 is a perspective view of the active element array of FIG. 24 in use on the wrist of a user.
Figure 27:
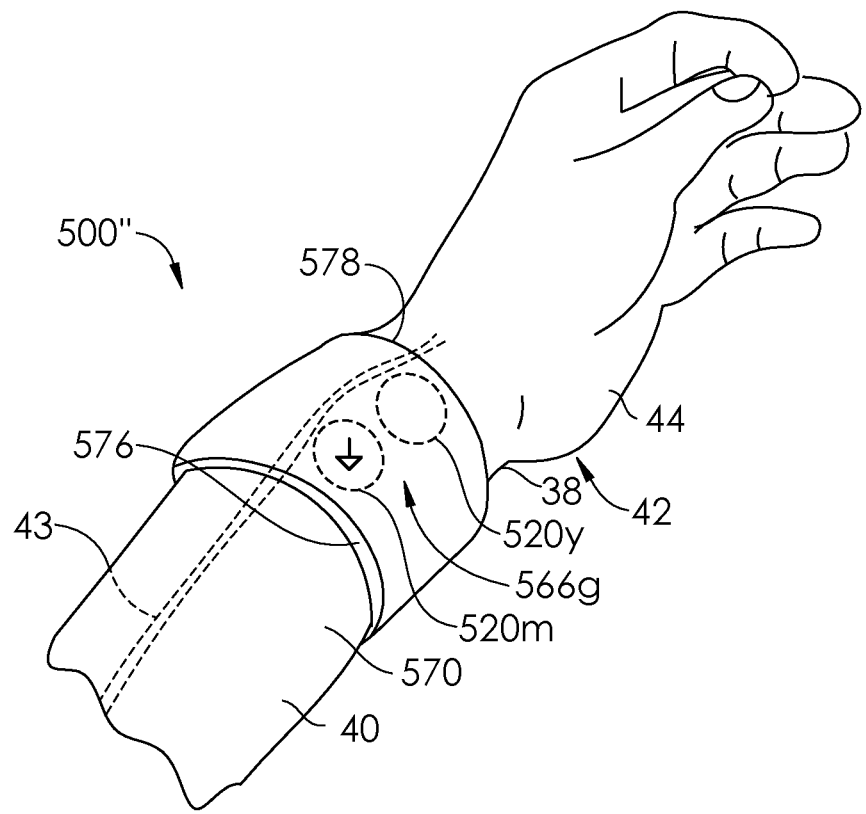
FIG. 27 is a perspective view of the active element array of FIG. 26 in use on the wrist of a user.

FIG. 22 illustrates a wearable blood pressure control system 500 having multi-mode energy delivery therapy including both vibration and electrical stimulation. The wearable blood pressure control system 500 is configured to be wrapped around a limb of a subject, as shown in FIGS. 25 and 27. A band 502 having a first end 504 and a second end 506 includes an inner-facing side 510 and an outer-facing side 512. The band 502 further includes an elastic clasp 508 having a first hook/loop area 514 configured to be secured to a second hook/loop area 516. The elastic clasp 508 comprises an elastic sheet configured to stretch longitudinally, such that the band 502 will fit on a variety of limb diameters. When the band 502 is secured to the limb, an additional band 518 maybe secured around the band 502 for additional securement, but in some embodiments, the band 502 alone is utilized. The additional band 518 may be similar to the second band 408 of FIG. 19, though without any of the active components (piezoelectric discs 478, electrodes 480). In some embodiments, the additional band 518 may comprise a band 404 having a bladder 416. The wearable blood pressure control system 500 includes eight conductive hydrogel electrodes 520 carried on the inner-facing side 510 of the band 502, and eight piezoelectric discs 522 (FIG. 28) embedded below the electrodes 520. The eight piezoelectric discs 522 are each acoustically coupled by the hydrogel such that they are able to be operable when the electrodes 520 are contacting the skin of the user. An adjustable internal surface 406 such as that of the wearable blood pressure control system 400 of FIG. 15 may alternatively be incorporated, and the two or more of the electrodes 520 may be used to measure impedance of the limb tissue, for an automatic inflation of the bladder 416, and automatic fitting optimization. A multi-terminal connector 524 includes magnetic clasps 526, 528 that are configured to magnetically locate a mating multi-terminal (e.g., multi-pin) connector, which may be attached to a smart watch, health tracker, fitness tracker, or a smart phone, or other mobile control system, such as a system carried on one's person or on clothing, or as part of the clothing. Multiple contacts 530 allow for various electrical connections in a small area. Sixteen contacts are shown, but any number is possible, including two to 32, four to sixteen, or six to twelve, for example. The pins of a multi-pin terminal may include spring-loaded electrical contact pins.

A receptable 560 is configured for placement of an electronic identification device, such as an RFID chip, an EPROM, an EEPROM, or a resistor for a Wheatstone Bridge.

Turning to FIG. 28, disc-shaped conductive hydrogel electrode 520 extends from the inner-facing side 510 of the band 502. The hydrogel electrode 520 can be flexible and stretchable, but these characteristics are less needed if the electrodes 520 are small. Thus, the size (e.g., diameter) of the electrodes 520 can be varied, depending on the particular geometry of the array. The electrode 520 is coupled to a first surface 534 of a flexible substrate 531 (e.g., polyimide flex circuit material) via a conductive paint 532. The conductive paint 532 is electrically connected to a trace 552 on the first surface 534 of the flexible substrate 531. In some embodiments, the conductive paint 532 comprises a silver-silver chloride (Ag—AgCl). In other embodiments, the conductive paint (ink) may comprise copper or gold, or other silver-based materials. A first portion 542 of a piezoelectric disc 536 is bonded to a first trace 546 on a second surface 538 of the flexible substrate 531 with a conductive epoxy 540. The piezoelectric disc 536 may comprise a PZT material (lead zirconate titanate (Pb[Zr(x)Ti(1−x)]O3)), or another appropriate ceramic material configured to vibrate in response to an applied voltage. A second portion 544 of the piezoelectric disc 536 is electrically coupled to a conductive tab 548 which in turn is electrically coupled to a second trace 550 on the second surface 538 of the flexible substrate 531. Thus, the electrode 520 is electrically coupled to a circuit on the first surface 534 of the flexible substrate and the piezoelectric disc 536 is electrically coupled to a circuit on the second surface 538 of the flexible substrate 531. The flexible substrate 531 may comprise one or more thin strips within the band 502 (for example, between an upper sheet 554 and a lower sheet 556 of the band 502 that are bonded together. Each element (electrode or piezoelectric) of each of the eight electrode 520/piezoelectric disc 536 layered pairs 558 may be operated independently, or in some instances, both elements of the layered pair 558 may be operated in unison.

Figure 24:
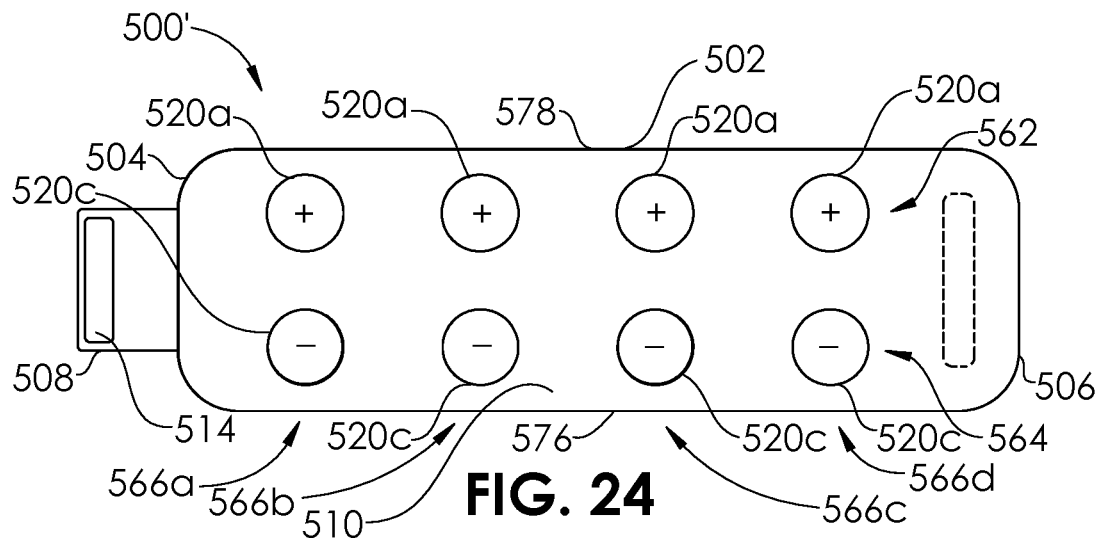
FIG. 24 is an active element array of the wearable blood pressure control system of FIGS. 22 and 23, according to an embodiment of the present disclosure.

The electrodes 520 may be electrically connected and arrayed on the band 502 in a variety of combinations in order to achieve a particular effect. In the wearable blood pressure control system 500' of FIGS. 24-25, the band 502 includes a first row 562 of four anode electrodes 520a and a second row 564 of four cathode electrodes 520c. When the band 502 is attached to the wrist 38 of a user 42, as in FIG. 25, each anode-cathode pair 566a-d is substantially aligned along the general longitudinal axis 568 of the median nerve 43, such that the application to the skin 570 of a negative charge from the cathodes 520c and the positive charge from the anodes 520a at substantially longitudinally-aligned locations 572, 574 is configured to create an effect on the conductive properties of the median nerve 43. In some cases, the conduction of the median nerve 43 is increased by the operation of the anode-cathode pair 566a-d, and in other cases, the conduction of the median nerve 43 is decreased or disrupted by the by the operation of the anode-cathode pair 566a-d. In use, a user may achieve acceptable results with the orientation of the band 502 as shown in FIG. 25, with a first lateral edge 576 of the band 502 located proximally and a second lateral edge 578 of the band 502 located distally. In other cases, the results may not be desirable, and the user my remove and reattach the band 502 such that the first lateral edge 576 of the band 502 is located distally and the second lateral edge 578 of the band 502 is located proximally, wherein the results are improved. The traces 552, 546, 550 for each electrode 520 and piezoelectric disc 536 of the flexible substrate 531 flex circuit 580 (FIG. 28) can be fabricated in a variety of patterns to achieve different electrical connections. The contacts 530 of the multi-terminal connector 524 may be assigned independently to also allow for different electrical connection configurations. Though the median nerve 43 is often the target, in other cases, the effect may be focused, or shared, on the radial nerve or the ulnar nerve. The band 502 may alternatively be located in other positions (around upper arm, around upper forearm) to get the desired effect, or even around a portion of the leg.

Figure 26:
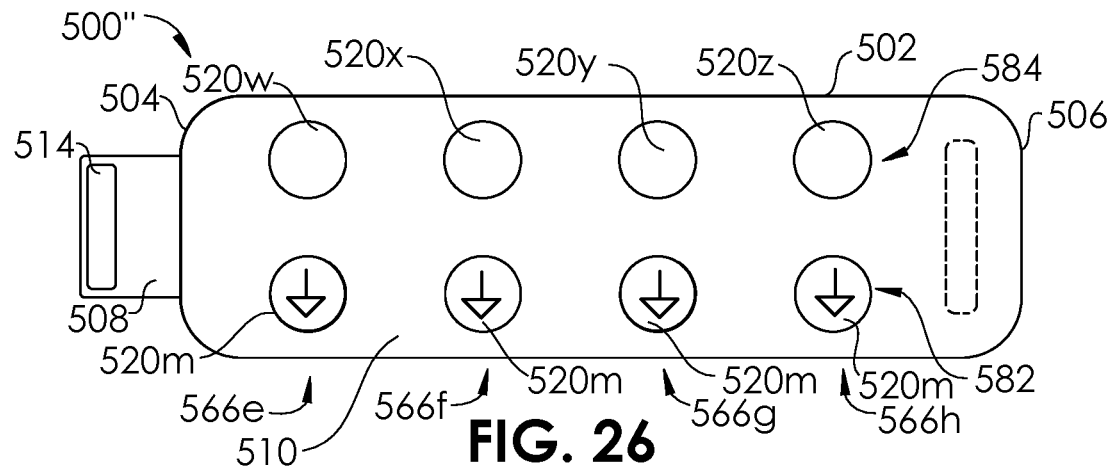
FIG. 26 is an active element array of the wearable blood pressure control system of FIGS. 22 and 23, according to an embodiment of the present disclosure.

In the wearable blood pressure control system 500" of FIGS. 26-27, the band 502 includes a first row 582 of four common-grounded electrodes 520m and a second row 584 of four electrodes 520w, 520x, 520y, 520z that are configured to be excited independently of each other. When the band 502 is attached to the wrist 38 of a user 42, as in FIG. 27, the common-grounded electrodes 520m are located proximally and each of the independent electrodes 520w-z are located distally. Because they are independently connected with respect to each other, the independent electrodes 520w-z can be operated in a wide range of different patterns.

In alternative embodiments, the electrodes 520 and piezoelectric discs 536 may each have unequal numbers (e.g., six electrodes 520 and four piezoelectric discs 536, etc.) or equal numbers. Some pairs 566 may exist in some portions of the band 502, while single electrodes 520 or single piezoelectric discs 536 may exist in other portions of the band 502. Though the bands 502 of the wearable blood pressure control systems 500, 500', 500" are shown without a bladder 416, in other embodiments, each of the wearable blood pressure control systems 500, 500', 500" may incorporate a bladder 416, either for one-size-fits-all sizing, or for sphygmomanometry, or for therapeutic compression. The arrays of electrodes 520 and piezoelectric discs 536 presented herein allow for multiple touch points on the skin or around the limb, which can lead to a faster reduction of blood pressure.

In alternative a wearable blood pressure control system 600 is illustrated in FIG. 29, and includes a housing 602 (similar to housing 402) and a band 604. The band 604 has a bracelet-like structure comprising five individual flex circuit sections 606a-e. The flex circuit sections 606a-e each have conductive tracings 608 coupled to components (e.g., electrodes, piezoelectric elements—not shown). The components may in some embodiments be arranged as in the layered pair 558 of FIG. 28. A hinge joint 610 between each adjacent flex circuit section 606a-e includes one or more conductor 612 linking them together electrically. The hinge joint 610 may in some embodiments include an elastic matrix, to allow some elastic separation and recoil (stretch) between adjacent flex circuit sections 606a-e. Though five flex circuit sections 606a-e are shown in FIG. 29, any number may be used, for example, between three and sixteen or between four and ten. The low-profile and light weight structure of the flex circuit sections 606a-e, as well as the modular architecture and ease of fabrication, increase affordability and allow for an easy to wear system.

Figure 23:
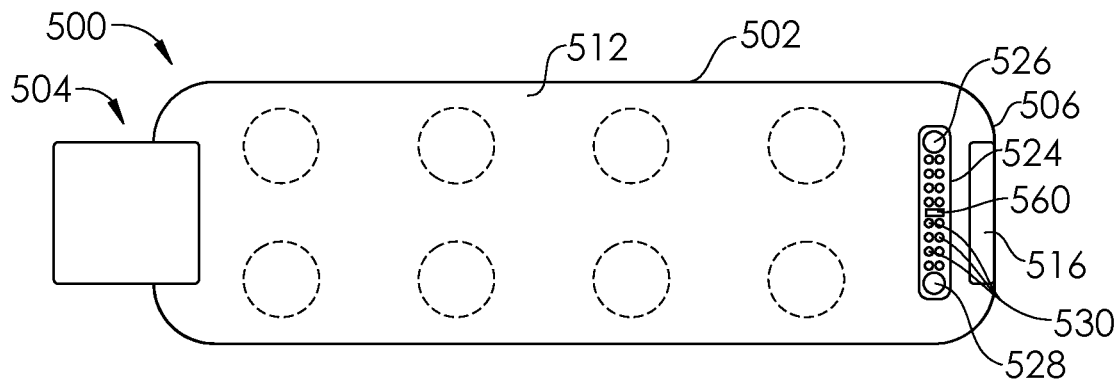
FIG. 23 is a bottom view of the wearable blood pressure control system of FIG. 22.

While the foregoing is directed to embodiments of the present invention, other and further embodiments of the invention may be devised without departing from the basic scope thereof. Though not described in detail above, the wearable blood pressure control system 400 of FIG. 15, the wearable blood pressure control system 500 of FIGS. 22-23, and the wearable blood pressure control system 600 of FIG. 29 may also be utilized according to the method described in relation to FIG. 14.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system for controlling blood pressure, comprising:
a wearable interface having an internal contact surface, the wearable interface configured to at least partially encircle a first portion of a first limb of a subject;
a sensor carried by the wearable interface and configured to be in proximity of the first portion of the first limb of the subject and to output a signal for determining at least a change in blood pressure of the subject at the first limb;
an energy applicator carried by the wearable interface and configured to apply therapeutic energy of two or more types to a deep nerve within the first limb of the subject; and
wherein the therapeutic energy of two or more types comprises vibrational energy and electrical stimulation energy.

2. The system of claim 1, wherein the sensor is further configured to measure electrocardiography data from the first limb of the subject.

3. The system of claim 2, wherein the sensor comprises a blood pressure sensor and an electrode configured to measure the electrocardiography data.

4. The system of claim 1, wherein the vibrational energy is provided by one or more piezoelectric elements of the energy applicator.

5. The system of claim 1, wherein the electrical stimulation energy is provided by one or more electrodes of the energy applicator.

6. The system of claim 5, wherein each of the one or more electrodes is configured to contact skin at the first portion of the first limb of the subject.

7. The system of claim 1, wherein the energy applicator comprises a hydrogel and is removably attachable to the wearable interface and configured to provide at least a portion of the internal contact surface of the wearable interface.

8. The system of claim 1, wherein the internal contact surface is adjustable to provide a functional fit on a variety of limb sizes.

9. The system of claim 8, further comprising a first electrode coupled to the internal contact surface at a first position and a second electrode coupled to the internal contact surface at a second position, the first and second electrodes configured to measure an impedance in the first portion of the first limb.

10. The system of claim 1, further comprising a first electrode coupled to the internal contact surface and a second electrode carried on an externally-facing surface of the system such that the first electrode is configured to contact skin at the first portion of the first limb of the subject, and the second electrode is configured to be contacted by skin from a portion of the subject other than the first limb of the subject.

11. The system of claim 10, wherein the first electrode and the second electrode are configured to obtain electrocardiography data from the subject when the first electrode contacts skin at the first portion of the first limb of the subject and the second electrode contacts skin from a digit of a second limb of the subject.

12. The system of claim 1, further comprising a controller configured to receive data from the sensor, and further configured to apply the therapeutic energy of two or more types to the deep nerve within the first limb of the subject in a first predetermined pattern, the first predetermined pattern at least partially determined by the data received from the sensor.

13. The system of claim 12, wherein the first predetermined pattern has a start time, a duration, and an end time.

14. The system of claim 13, wherein at least a portion of the duration of the first predetermined pattern comprises applying the vibrational energy and electrical stimulation energy simultaneously.

15. The system of claim 13, wherein the duration of the first predetermined pattern is less than about 15 minutes.

16. The system of claim 12, wherein the controller is configured to modify operation of the energy applicator over time.

17. The system of claim 16, wherein the modification of the operation of the energy applicator is based on at least some measured changes in cardiovascular parameters in the subject.

18. The system of claim 1, wherein the sensor is an inflatable cuff configured to compress one or more arteries in the limb of the subject.

19. The system of claim 1, wherein the sensor comprises a hydrogel and is removably attachable to the wearable interface and configured to provide at least a portion of the internal contact surface of the wearable interface.

20. The system of claim 1, wherein the sensor comprises at least one modality selected from the list consisting of: photoplethysmography and ultrasound.

21. The system of claim 1, wherein the first limb comprises an arm and the deep nerve comprises a median nerve.

22. The system of claim 1, wherein the first limb comprises an arm and the deep nerve comprises a radial nerve.

23. The system of claim 1, wherein the first limb comprises an arm and the deep nerve comprises an ulnar nerve.

24. The system of claim 4, wherein at least one of the one or more piezoelectric elements of the energy applicator is configured to vibrate at a frequency of between about 20 kHZ and about 1 MHz.

25. The system of claim 4, wherein at least one of the one or more piezoelectric elements of the energy applicator is configured to vibrate at a frequency of between about 20 kHZ and about 700 kHz.

* * * * *